US004001700B2

United States Statutory Invention Registration [19]

[11] Reg. Number: H1700

Morishima et al.

[45] Published: Dec. 2, 1997

[54] DEVELOPING AGENT FOR SILVER HALIDE PHOTOGRAPHIC MATERIAL, DEVELOPING SOLUTION COMPOSITION AND METHOD FOR DEVELOPING SILVER HALIDE PHOTOGRAPHIC MATERIAL

[75] Inventors: Shinnichi Morishima; Kiyoshi Morimoto, both of Kanagawa, Japan

[73] Assignee: Fuji Photo Film Co., Ltd., Minami-ashigara, Japan

[21] Appl. No.: 748,091

[22] Filed: Nov. 12, 1996

Related U.S. Application Data

[62] Division of Ser. No. 551,288, Oct. 31, 1995, abandoned.

[30] Foreign Application Priority Data

Nov. 2, 1994 [JP] Japan ..... 6-269832

[51] Int. Cl.[6] ..... G03C 5/00

[52] U.S. Cl. ..... 430/436

[58] Field of Search ..... 430/440, 446, 430/480, 483, 264

[56] References Cited

U.S. PATENT DOCUMENTS

| | | | |
|---|---|---|---|
| 3,337,342 | 8/1967 | Green | 430/249 |
| 5,098,819 | 3/1992 | Knapp | 430/440 |
| 5,236,816 | 8/1993 | Purol et al. | 430/492 |
| 5,419,997 | 5/1995 | Hirano | 430/264 |
| 5,474,879 | 12/1995 | Fitterman et al. | 430/440 |
| 5,478,697 | 12/1995 | Sakai et al. | 430/264 |
| 5,503,965 | 4/1996 | Okutsu | 430/440 |
| 5,508,152 | 4/1996 | Toyoda et al. | 430/441 |

FOREIGN PATENT DOCUMENTS

| | | |
|---|---|---|
| 681408 | 11/1966 | Belgium . |
| 0148094 | 7/1985 | European Pat. Off. . |
| 0506235 | 9/1992 | European Pat. Off. . |
| 4364182 | 12/1992 | Japan . |
| 6194790 | 7/1994 | Japan . |
| 9308295 | 4/1993 | WIPO . |

*Primary Examiner*—Charles T. Jordan
*Assistant Examiner*—Meena Chelliah
*Attorney, Agent, or Firm*—Sughrue, Mion, Zinn, Macpeak & Seas, PLLC

[57] ABSTRACT

A silver halide photographic material is processed with a developing solution containing at least one kind of developing agent represented by the following general formula (A):

(A)

wherein $R_1$ and $R_2$ may be the same or different, and each represents a hydrogen atom or a substituent group, with the proviso that $R_1$ and $R_2$ are not methyl groups at the same time nor a combination of a hydrogen atom and a methyl group, thereby providing a novel method for forming an image by use of the developing solution not using a dihydroxybenzene compound as the developing agent, and more particularly a superhigh contrast negative image by use of the photographic material containing a hydrazine compound.

5 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DEVELOPING AGENT FOR SILVER HALIDE PHOTOGRAPHIC MATERIAL, DEVELOPING SOLUTION COMPOSITION AND METHOD FOR DEVELOPING SILVER HALIDE PHOTOGRAPHIC MATERIAL

This is a divisional of application Ser. No. 08/551,288 filed Oct. 31, 1995.

FIELD OF THE INVENTION

The present invention relates to a method for processing a silver halide photographic material and a developing solution composition, and particularly to a method for forming am image on a silver halide photographic material by use of a developing solution substantially free from a dihydroxybenzene developing agent.

BACKGROUND OF THE INVENTION

Silver halide photographic materials have been utilized in various fields such as a plate making field and a medical diagnostic field. As the fields of utilization have been enlarged and deepened, requirements for developing steps necessary for image formation have been increased. In particular, rapid and stable processing has been strongly desired.

The silver halide photographic materials are generally treated in the steps of development, fixing and washing, after exposure. In particular, a black-and-white developing solution is generally an alkaline solution containing hydroquinone, a dihydroxybenzene compound, as a developing agent, an aminophenol derivative or a 3-pyrazolidone derivative as an auxiliary developing agent, and a sulfite. It is also well known that enediols such as ascorbic acid, in addition to dihydroxybenzene compounds, function as developing agents. Such enediols have recently occupied attention as the above-mentioned developing agents having no ecological or toxicological problem. For example, U.S. Pat. Nos. 2,688,549 and 3,826,654 disclose that image formation is possible under high-alkaline conditions of at least pH 12. However, these image forming processes can not provide images high in contrast.

Some attempts have been made to increase the contrast in a developing system using ascorbic acid. For example, Zwicky describes that use of ascorbic acid as a sole developing agent generates a kind of lith effect (*J. Phot. Sci.*, 27, 185 (1979)). However, this system was considerably low in contrast, compared with the hydroquinone developing system. Further, U.S. Pat. No. T896,022 and JP-B-49-46939 (the term "JP-B" as used herein means an "examined Japanese patent publication") disclose a system in which ascorbic acid is used in combination with a bis(quaternary ammonium salt). However, although this system shows the effect of enhancing development, the effect of increasing the contrast is scarcely observed. Further, JP-A-3-249756 (the term "JP-A" as used herein means an "unexamined published Japanese patent application) and JP-A-4-32838 also describe the effect of ascorbic acid and a quaternary salt used in combination. However, the contrast of images obtained is insufficient. Furthermore, JP-A-5-88306 discloses that the high contrast is obtained by using ascorbic acid as a sole developing agent and maintaining the pH at 12.0. However, such a developing solution is significantly deteriorated by air oxidation, producing a large problem for the stability of the developing solution.

In addition, an example is described in which a developing system high in sensitivity and low in stain and fog can be obtained by using a special developing solution mainly containing ascorbic acid and a hydrazine derivative (U.S. Pat. No. 3,730,727). However, it does not refer to contrast enhancement at all.

It is well known to process hydrazine-containing photographic materials with ascorbic acid developing solutions, as described in U.S. Pat. No. 5,236,816 and WO 93/11456, but both are insufficient in respect to the contrast. In the latter, hard gradation enhancement is conducted by the addition of an amine to the developing solution. This is environmentally unfavorable. A processing method for obtaining a high-contrast image using toxicologically preferred ascorbic acid has been desired, but the sufficient hard gradation has not been obtained. Further, use of the ascorbic acid developing agents causes a marked decrease in pH due to deterioration by air oxidation and noticeably reduced photographic characteristics, resulting in a practical problem. Furthermore, hard images required for printing plate making films necessitate processing with developing solutions having a relatively high pH of 11 or more, and the air oxidation stability has not been sufficient.

SUMMARY OF THE INVENTION

It is therefore an object of the present invention to provide a novel method for forming an image by use of a developing solution not using a dihydroxybenzene compound as a developing agent, and more particularly to provide a super-high contrast negative image by use of a photographic material containing a hydrazine compound.

To provide a novel method for forming an image by use of a developing solution of the present invention not using a dihydroxybenzene compound as a developing agent was attained by a developing agent represented by the following general formula (A), a developing solution composition containing at least one kind of said developing agent, and a method for processing a silver halide photographic material comprising processing the silver halide photographic material exposed with a developing solution free from a dihydroxybenzene compound and containing at least one kind of developing agent of general formula (A) as a developing agent:

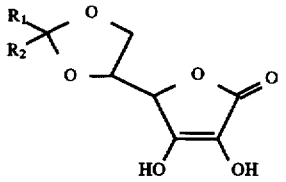

(A)

wherein $R_1$ and $R_2$ may he the same or different, and each represents a hydrogen atom or a substituent group, with the proviso that $R_1$ and $R_2$ are not methyl groups at the same time nor a combination of a hydrogen atom and a methyl group.

DETAILED DESCRIPTION OF THE INVENTION $R_1$ and $R_2$ of a compound represented by general formula (A) are described in detail below.

In the formula, examples of the substituent groups represented by $R_1$ and $R_2$ include alkyl groups, alkenyl groups, aryl groups, halogen atoms, alkoxy groups, aryloxy groups, alkylthio groups, arylthio groups, acyl groups, oxycarbonyl groups, carbamoyl groups, a carboxyl group (containing salts thereof), a sulfo group (containing salts thereof) and heterocyclic groups, and $R_1$ and $R_2$ may combine together to form ring structures composed of carbon atoms, nitrogen atoms, oxygen atoms or sulfur atoms. These groups may be further substituted if possible, and the substituent groups include alkyl groups, alkenyl groups, aryl groups, halogen atoms, a cyano group, a nitro group, a hydroxyl group, alkoxy groups, aryloxy groups, alkylthio groups, arylthio groups, acyloxy groups, an amino group, alkylamino groups, carbonamido groups, sulfonamido groups, ureido groups, acyl groups, oxycarbonyl groups, carbamoyl groups, sulfonyl groups, sulfamoyl groups, a carboxyl group (containing salts thereof), a sulfo group (containing salts thereof), a hydroxyamino group and heterocyclic groups.

Examples of the substituent groups represented by $R_1$ and $R_2$ are shown in more detail. The alkyl groups are preferably straight, branched or cyclic chain alkyl groups each having 1 to 7 carbon atoms. Examples thereof include methyl, ethyl, propyl, i-propyl, butyl, t-butyl, benzyl, bromomethyl, trifluoromethyl, dihydroxymethyl, methoxymethyl, benzyloxymethyl, 2-methoxyethyl, 2-methylthioethyl, phenylthiomethyl, 1,2-diacetoxyethyl, aminomethyl, acetamidomethyl, methanesulfonamidomethyl, ureidomethyl, 2-acetylethyl, methoxycarbonylmethyl, 2-methoxycarbonylethyl, carbamoylmethyl, 2-benzenesulfonylethyl, sulfamoylmethyl, 2-carboxyethyl and 1-hydroxyamino-1-methylethyl. The alkenyl groups are preferably straight or branched chain alkenyl groups each having 2 to 7 carbon atoms. Examples thereof include ethenyl, 1-propenyl, 2-butenyl and 2-pentenyl. The aryl groups are preferably aryl groups each having 6 to 10 carbon atoms. Examples thereof include phenyl, p-methylphenyl, p-ethenylphenyl, m-fluorophenyl, m-nitrophenyl, p-hydroxyphenyl, anisyl, p-acetoxyphenyl, p-dimethylaminophenyl, p-aminophenyl, m-formylphenyl, p-methoxycarbonylphenyl, p-carboxyphenyl and m-sulfophenyl. The halogen atoms are preferably a fluorine atom and a chlorine atom.

The alkoxy groups are preferably straight or branched chain alkoxy groups each having 1 to 7 carbon atoms. Examples thereof include methoxy, ethoxy, propoxy, butoxy, pentyloxy, hexyloxy and 2-methoxyethoxy. The aryloxy groups are preferably aryloxy groups each having 6 to 10 carbon atoms, which include phenoxy, p-methylphenoxy, p-hydroxyphenoxy, o-carboxyphenoxy and o-sulfophenoxy. The alkylthio groups are preferably straight or branched chain alkylthio groups each having 1 to 7 carbon atoms. Examples thereof include methylthio, ethylthio and hexylthio. The arylthio groups are preferably arylthio groups each having 6 to 10 carbon atoms. Examples thereof include phenylthio and 4-hydroxyphenylthio.

The acyl groups are preferably acyl groups each having 1 to 7 carbon atoms. Examples thereof include formyl, acetyl, propionyl and benzoyl. The oxycarbonyl groups are preferably oxycarbonyl groups each having 1 to 7 carbon atoms. Examples thereof include methoxycarbonyl and ethoxycarbonyl. The carbamoyl groups are preferably carbamoyl groups each having 1 to 7 carbon atoms. Examples thereof include carbamoyl, N-trifluoromethylcarbamoyl and N,N-dimethylcarbamoyl. The heterocyclic groups are heterocyclic groups of 5- to 6-membered rings composed of carbon atoms, nitrogen atoms, oxygen atoms or sulfur atoms, and the 5- to 6-membered rings may form saturated or unsaturated condensed rings. Examples thereof include furyl, benzofuryl, pyranyl, pyrrolyl, imidazolyl, indazolyl, pyrazolyl, triazolyl, pyridyl, pyrimidyl, pyridazyl, thienyl and isathiazolyl. Furyl, pyridyl, pyrimidyl and thienyl are preferred. Further, the ring structures which $R_1$ and $R_2$ combine to form and which are composed of carbon atoms, nitrogen atoms, oxygen atoms or sulfur atoms include cyclopentyl, cyclohexyl, chromanyl, pyrrolidinyl, pyrrolinyl, imidazolidinyl, imidazolinyl, pyrazolidinyl, piperidyl, piperadinyl and indolinyl. Cyclopentyl, cyclohexyl, chromanyl and piperidyl are preferred.

These groups may be further substituted if possible.

In the formula (A), the substituent groups represented by $R_1$ and $R_2$ are particularly preferably hydrogen atoms, or substituted or unsubstituted alkyl, alkenyl or aryl groups, more preferably hydrogen atoms, or substituted or unsubstituted alkyl groups, and most preferably substituted or unsubstituted alkyl groups. The substituent groups include alkyl groups, alkenyl groups, aryl groups, halogen atoms, a hydroxyl group, alkoxyl groups, a carboxyl group (containing salts thereof), a sulfo group (containing salts thereof) and a hydroxyamino group. $R_1$ and $R_2$ may be the same or different, and each represents a hydrogen atom or a substituent group, but they are not methyl groups at the same time nor a combination of a hydrogen atom and a methyl group.

The compounds of general formula (A) are described in the so-called enol form. However, isomeric compounds thereof in the keto form are the same compounds in effect, and compounds in which hydrogen atoms are isomerized are included in the claims of the present invention.

Examples of the compounds of the present invention include, but are not limited to the following compounds:

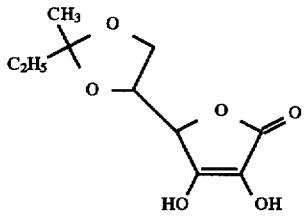

A-1

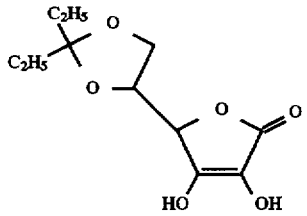

A-2

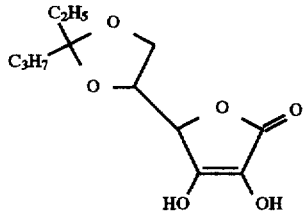

A-3

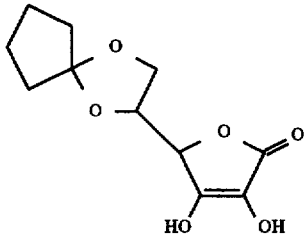

A-4

-continued
A-5
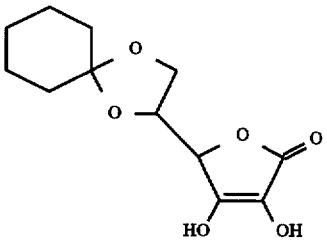
A-6
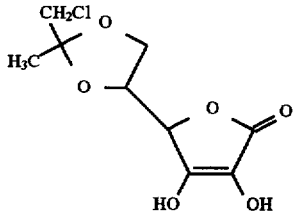
A-7
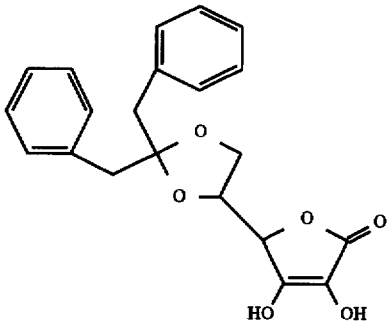
A-8
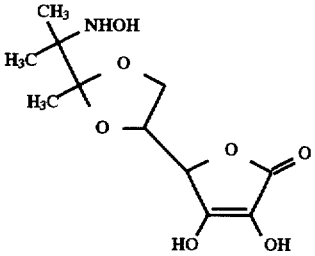
A-9
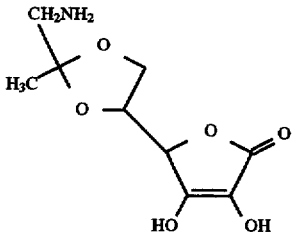
A-10
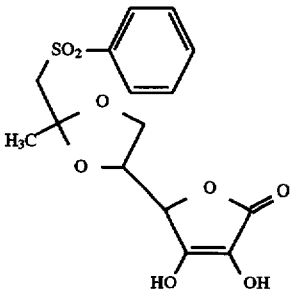
-continued
A-11
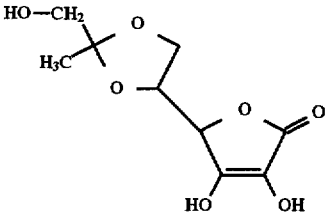
A-12
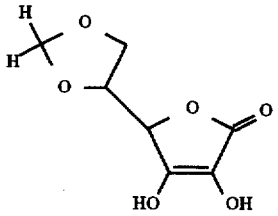
A-13
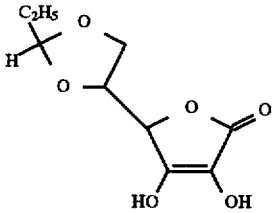
A-14
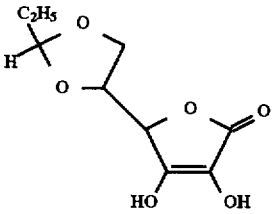
A-15
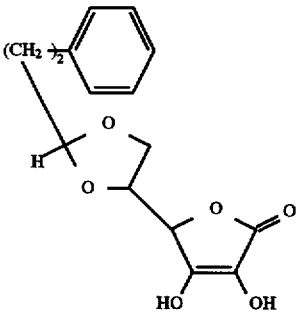
A-16
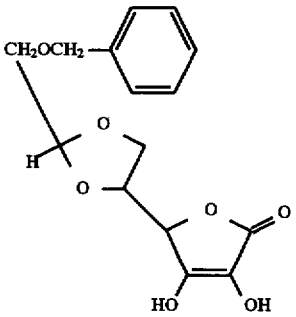

-continued
A-17
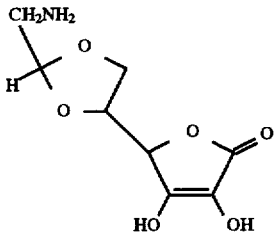
A-18
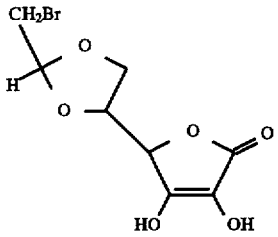
A-19
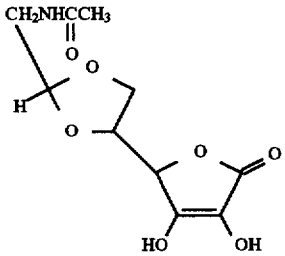
A-20
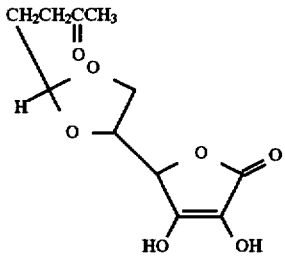
A-21
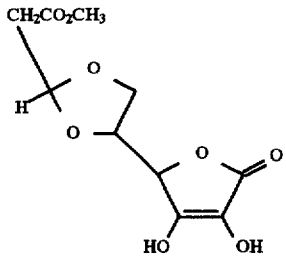
A-22
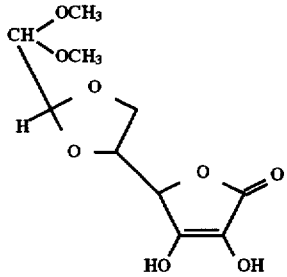
-continued
A-23
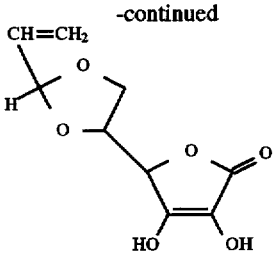
A-24
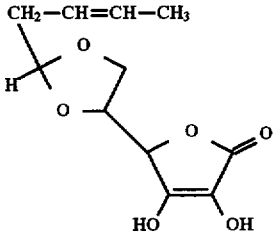
A-25
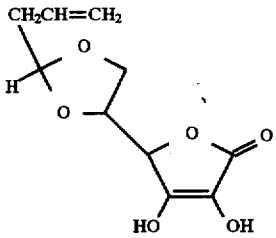
A-26
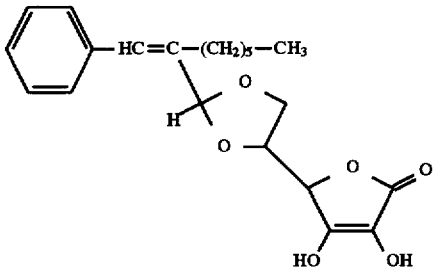
A-27
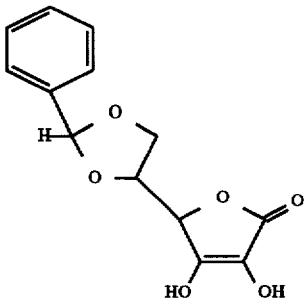
A-28
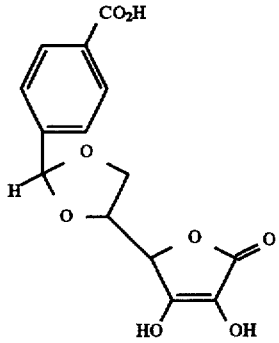

-continued
A-29
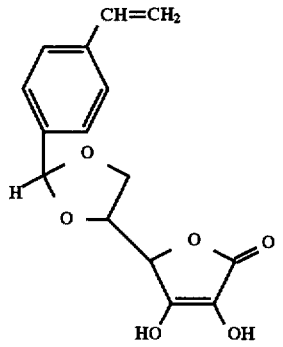
A-30
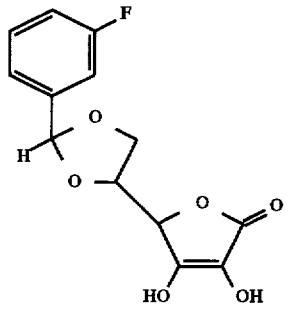
A-31
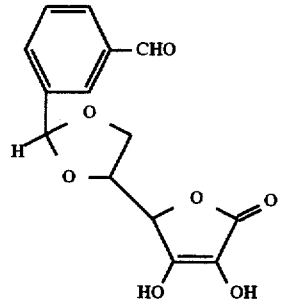
A-32
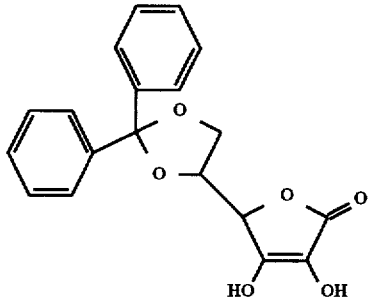
A-33
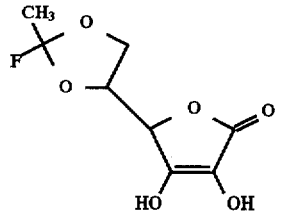
-continued
A-34
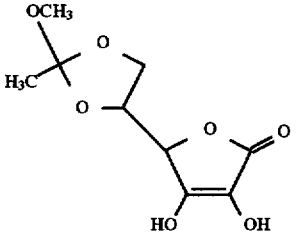
A-35
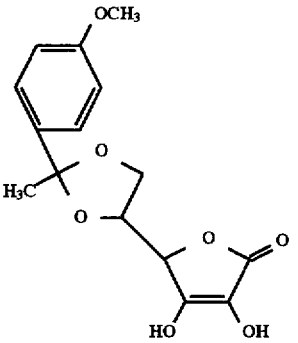
A-36
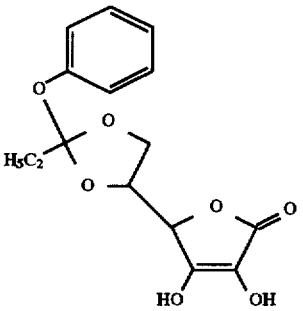
A-37
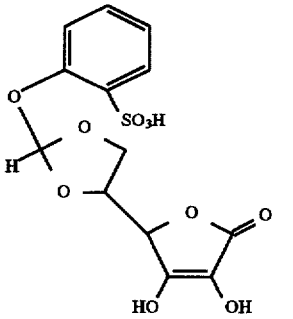
A-38
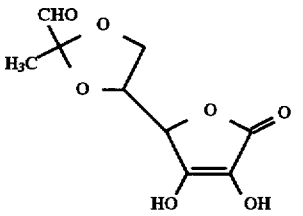

-continued
A-39
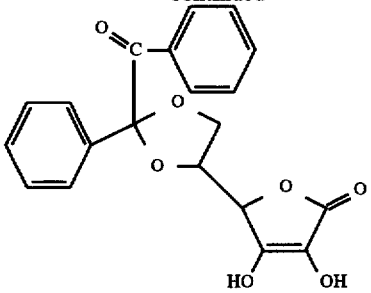
A-40
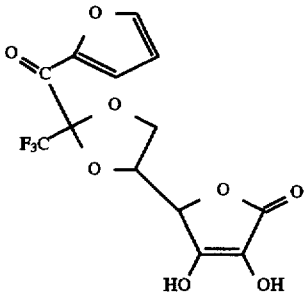
A-41
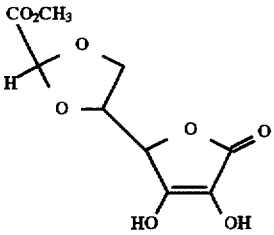
A-42
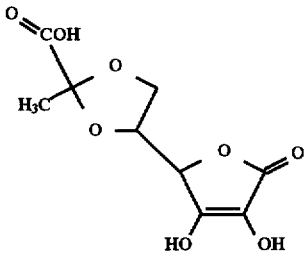
A-43
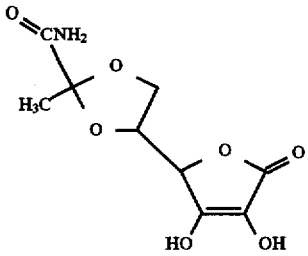
A-44
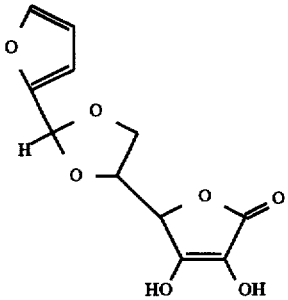
-continued
A-45
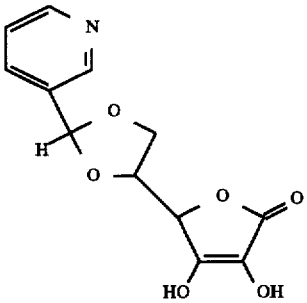
A-46
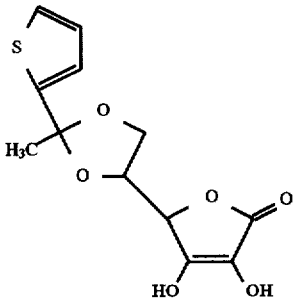
A-47
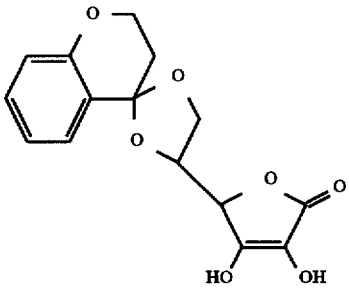
A-48
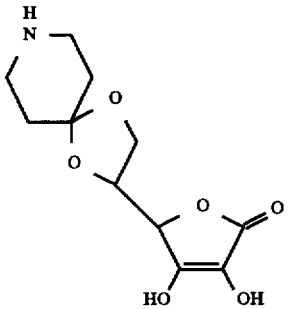
A-49
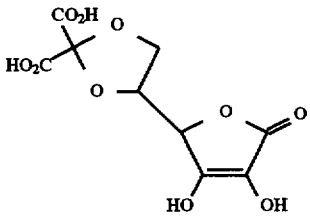

-continued

A-50

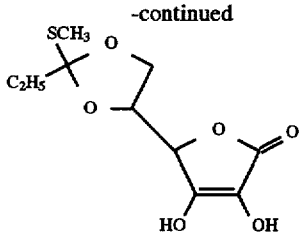

A-51

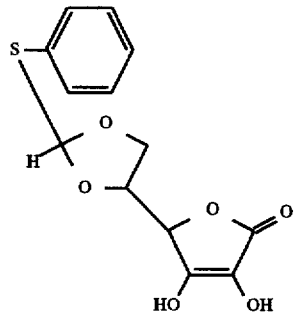

A-52

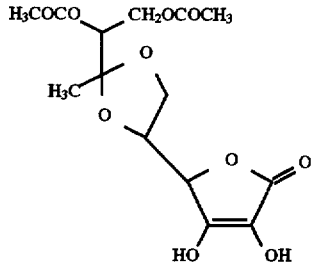

A-53

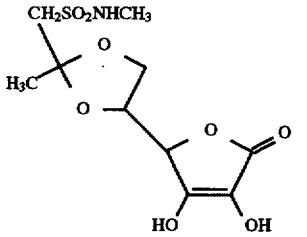

A-54

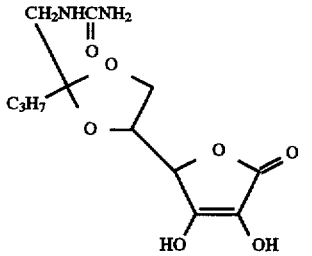

A-55

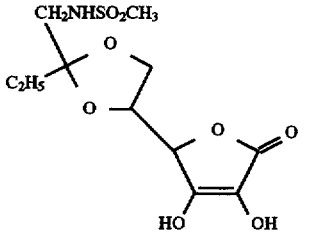

The compounds represented by general formula (A) can be synthesized in accordance with the general synthesis methods described in A. Klausener, H. Frauenrath, W. Lange, G. K. Mikhail, S. Schneider and D. Schroder, *Methoden der Organischen Chemie,* vol. 14a/1, 133–301 (1991), JP-A-60-139619, JP-A-60-69079 and JP-A-4-364182. The amount of the compounds represented by general formula (A) used generally ranges from $5\times10^{-3}$ mol to 1 mol per liter of developing solution, and preferably from $10^{-2}$ mol to 0.5 mol per liter of developing solution.

Further, the plurality of compounds described above can also be used in combination.

Examples of 1-phenyl-3-pyrazolidone and derivative thereof as auxiliary developing agents include 1-phenyl-3-pyrazolidone, 1-phenyl-4,4-dimethyl-3-pyrazolidone, 1-phenyl-4-methyl-4-hydroxymethyl-3-pyrazolidone, 1-phenyl-4,4-dihydroxymethyl-3-pyrazolidone, 1-phenyl-5-methyl-3-pyrazolidone, 1-p-aminophenyl-4,4-dimethyl-3-pyrazolidone and 1-p-tolyl-4-methyl-4-hydroxymethyl-3-pyrazolidone.

p-Aminophenol auxiliary developing agents include N-methyl-p-aminophenol, p-aminophenol, N-(β-hydroxyethyl)-p-aminophenol, N-(4-hydroxyphenyl) glycine, 2-methyl-p-aminophenol and p-benzylaminophenol. Of these, N-methyl-p-aminophenol is preferred.

When the developing agent is used in combination with the 1-phenyl-3-pyrazolidone compound or the p-aminophenol compound, it is preferred to use the latter usually in an amount of $10^{-3}$ mol/liter to 0.1 mol/liter, more preferably in an amount of $10^{-3}$ mol/liter to 0.06 mol/liter.

In the present invention, "substantially free from a dihydroxybenzene compound" means that the concentration of the dihydroxybenzene compound in the developing solution is insignificant (for example, $5\times10^{-4}$ mol/liter or less) compared with the amount of the compound of general formula (A) or the above-mentioned auxiliary developing agent. The developing solution of the present invention preferably contains no dihydroxybenzene compound at all.

Sulfites such as sodium sulfite, potassium sulfite, lithium sulfite, sodium bisulfite, potassium metabisulfite and sodium formaldehydebisulfite, or hydroxylamine compounds such as hydroxylamine sulfate, hydroxylamine hydrochloride, monomethylhydroxylamine hydrochloride and diethylhydroxylamine may be added to the developing solutions of the present invention as preservatives. The sulfites and the hydroxylamine compounds are used in an amount of 0.01 mol/liter or more. If the sulfites are used in large amounts, they dissolve silver halide emulsion grains, causing silver stain and increased COD (chemical oxygen demand). Hence, the amount of the sulfites added should be minimized.

The pH of the developing solutions used in processing preferably ranges from 9 to 12, and more preferably from 9 to 11.

Alkaline agents used for establishment of the PH may contain pH regulators such as sodium hydroxide, potassium hydroxide, sodium carbonate, potassium carbonate, sodium tertiary phosphate and potassium tertiary phosphate.

Dialdehyde hardening agents or bisulfite addition products thereof may be used in the developing solutions, and examples thereof include glutaraldehyde and bisulfite addition products thereof.

Additives used in addition to the above include development inhibitors such as sodium bromide and potassium bromide; organic solvents such as ethylene glycol, diethylene glycol, triethylene glycol and dimethylformamide; and development accelerators such as alkanolamines such as diethanolamine and triethanolamine, imidazole or derivatives thereof. Mercapto compounds, indazole compounds, benzotriazole compounds and benzoimidazole may be contained as antifoggants or black pepper inhibitors. Examples thereof include 5-nitroindazole, 5-p-nitrobenzoylaminoindazole, 1-methyl-5-nitroindazole, 6-nitroindazole, 3-methyl-5-nitroindazole, 5-nitrobenzindazole, 2-isopropyl-5-nitrobenzimidazole, 5-nitrobenzotriazole, sodium 4-[(2-mercapto-1,3,4-thiadiazole-2-yl)thio]butanesulfonate, 5-amino-1,3,4-thiadiazole-2-thiol, methylbenzotriazole, 5-methylbenzotriazole and 2-mercaptobenzotriazole. The amount of these antifoggants is usually 0.01 to 10 mmol per liter of developing solution, and more preferably 0.1 to 2 mmol.

Further, in the developing solutions of the present invention, various kinds of organic and inorganic chelating agents can be used in combination. As the inorganic chelating agents, sodium tetrapolyphosphate, sodium hexametaphosphate, etc. can be used.

On the other hand, as the organic chelating agents, organic carboxylic acids, aminopolycarboxylic acids, organic phosphonic acids, aminophosphonic acids and organic phosphonocarboxylic acids can be mainly used.

The organic carboxylic acids include but are not limited to acrylic acid, oxalic acid, malonic acid, succinic acid, glutaric acid, adipic acid, pimelic acid, azelaic acid, sebacic acid, nonanedicarboxylic acid, decanedicarboxylic acid, undecanedicarboxylic acid, maleic acid, itaconic acid, malic acid, citric acid and tartaric acid.

The aminopolycarboxylic acids include iminodiacetic acid, nitrilotriacetic acid, nitrilotripropionic acid, ethylenediaminemonohydroxyethyltriacetic acid, ethylenediaminetetra-acetic acid, glycolethertetraacetic acid, 1,2-diaminopropane-tetraacetic acid, diethylenetriaminepentaacetic acid, triethylenetetraminehexaacetic acid, 1,3-diamino-2-propanoltetraacetic acid, glycoletherdiaminetetraacetic acid and compounds described in JP-A-52-25632, JP-A-55-67747, JP-A-57-102624 and JP-B-53-40900.

The organic phosphonic acids include hydroxyalkylidenediphosphonic acids described in U.S. Pat. Nos. 3,214,454 and 3,794,591 and West German Patent (OLS) 2227639, and compounds described in *Research Disclosure,* 181, Item 18170 (May, 1979).

The aminophosphonic acids include compounds described in *Research Disclosure,* 18170 described above, JP-A-57-208554, JP-A-54-61125, JP-A-55-29883 and JP-A-56-97347, as well as aminotris(methylenephosphonic acid), ethyleneaminetetra-methylenephosphonic acid and aminotrimethylenephosphonic acid.

The organic phosphonocarboxylic acids include compounds described in JP-A-52-102726, JP-A-53-42730, JP-A-54-121127, JP-A-55-4024, JP-A-55-4025, JP-A-55-126241, JP-A-55-65955, JP-A-55-65956 and *Research Disclosure,* 18170 described above.

These chelating agents may be used in the form of alkali metal salts or ammonium salts. The amount of these chelating agents added is preferably $1\times10^{-4}$ to $1\times10^{-1}$ mol per liter of developing solution, and more preferably $1\times10^{-3}$ to $1\times10^{-2}$ mol.

Further, compounds described in JP-A-56-24347, JP-B-56-46585, JP-B-62-2849 and JP-A-4-362942 can be used in the developing solutions as silver stain inhibitors.

Furthermore, compounds described in JP-A-62-212651 can be used as developer streak preventives, and compounds described in JP-A-61-267759 can be used as dissolving aids.

In addition, the developing solutions may contain color toning agents, surfactants, defoaming agents and hardening agents as so desired.

In the developing solutions used in the present invention, carbonates, boric acid described in JP-A-62-186259, saccharides described in JP-A-60-93433 (for example, saccharose), oximes (for example, acetoxime), phenols (for example, 5-sulfosalicylic acid) and tertiary phosphates (for example sodium salt and potassium salt) are used as buffers, and carbonates are preferably used.

The processing temperature and time are related to each other, and determined with reference to the whole processing time. The processing temperature is generally about 20° C. to about 50° C., and preferably 25° to 45° C., and the processing time is 5 seconds to 2 minutes, and preferably 7 seconds to 1 minute and 30 seconds.

When one meter square of a silver halide black-and-white photographic material is processed, the replenisher volume of the developing solution is 500 ml or less, and preferably 400 ml or less.

For the purpose of reducing transport costs of processing solutions, packaging material costs and space, it is preferred that the processing solution are concentrated and diluted at the time of use to use them. In order to concentrate the developing solutions, it is effective that salt components contained in the developing solutions are potassium salts.

In the developing solutions of the present invention, amino compounds such as alkanolamines described in European Patent Publication No. 136582, British Patent 958678, U.S. Pat. No. 3,232,761, JP-A-56-106244, JP-A-50-106244, JP-A-61-267759 and JP-A-2-208652 can be used for development acceleration, an increase in contrast and other purposes.

In addition, compounds described in L. F. A. Mason, *Photographic Processing Chemistry,* pages 226 to 229 (Focal Press, 1966), U.S. Pat. Nos. 2,193,015 and 2,592,364 and JP-A-48-64933 may be used.

As methods for preparing the solutions of processing agents, methods described in JP-A-61-177132, JP-A-3-134666 and JP-A-3-67258 can be used. As replenishing methods, methods described in JP-A-5-216180 can be used.

Fixing solutions used in a fixing step are aqueous solutions containing sodium thiosulfate or ammonium thiosulfate, and tartaric acid, citric acid, gluconic acid, boric acid, iminodiacetic acid, 5-sulfosalicylic acid, glucoheptanoic acid, Tiron, ethylenediaminetetraacetic acid, diethylenetriaminepentaacetic acid, nitrilotriacetic acid or salts thereof, if necessary. From the recent viewpoint of environmental conservation, it is preferred that boric acid is not contained.

Fixing agents of the fixing solutions are sodium thiosulfate, ammonium thiosulfate, etc., and ammonium thiosulfate is preferred in terms of fixing speed. However, from the recent viewpoint of environmental conservation, sodium thiosulfate is preferred. The amount of these known fixing agents used can be appropriately changed, and it is generally about 0.1 to about 2 mol/liter and particularly preferably 0.2 to 1.5 mol/liter.

The fixing solutions can contain hardening agents (for example, water-soluble aluminum compounds), preservatives (for example, sulfites and bisulfites), pH buffers (for example, acetic acid), pH regulators (for example, ammonium and sulfuric acid), chelating agents, surfactants, wetting agents and fixing accelerators if desired.

The surfactants include, for example, anionic surfactants such as sulfated compounds and sulfonated compounds, polyethylene surfactants and amphoteric surfactants described in JP-A-57-6740. Further, known defoaming agents may be added. The wetting agents include, for example, alkanolamines and alkylene glycols. The fixing accelerators include, for example, thiourea derivatives described in JP-B-45-35754, JP-B-58-122535 and JP-B-58-122536, alcohols having triple bonds in their molecules, thioether compounds described in U.S. Pat. No. 4,126,459 and mesoionic compounds described in JP-A-4-229860. Further, compounds described in JP-A-2-44355 may also be used.

As the pH buffers, for example, organic acids such as acetic acid, malic acid, succinic acid, tartaric acid, citric acid, oxalic acid, maleic acid, glycolic and adipic acid, and inorganic buffers such as boric acid, phosphates and sulfites can be used. Acetic acid, tartaric acid and sulfites are preferably used.

The pH buffers are used herein to prevent the pH of the fixing agents from increasing due to introduction of the developing solutions, and used in an amount of about 0.01 to 1.0 mol/liter, more preferably about 0.02 to 0.6 mol/liter.

Further, as dye elution accelerators, compounds described in JP-A-64-4739 can also be used.

The hardening agents in the fixing solutions of the present invention include water-soluble aluminum salts and chromium salts. Preferred compounds are water-soluble aluminum salts, and examples thereof include aluminum chloride, aluminum sulfate and potassium alum. The amount added is preferably 0.01 mol to 0.2 mol/liter, and more preferably 0.03 to 0.08 mol/liter.

The fixing temperature is about 20° C. to about 50° C., and preferably 25° to 45° C., and the fixing time is 5 seconds to 1 minute, and preferably 7 seconds to 50 seconds.

The replenishment rate of the fixing solutions is 600 ml/m$^2$ or less based on the amount of photographic material processed, and preferably 500 ml/m$^2$ or less.

The photographic materials which have been developed and fixed are then subjected to washing and stabilization processing.

Washing and stabilization processing are conducted in a washing water amount of 20 liters or less per m$^2$ of silver halide photographic material, and can also be conducted at a replenishment rate of 3 liters or less (including 0, namely pool washing). That is, not only water-saving processing becomes possible, but also piping for installation of an automatic processor can be made unnecessary.

As a method for decreasing the replenishment rate of washing water, a multi-stage countercurrent system (for example, two-stage, three-stage, etc.) has been known for long. When this multi-stage countercurrent system is applied to the present invention, the photographic material after fixing is gradually processed in a normal direction, namely successively coming into contact with a processing solution not contaminated with a fixing solution, which results in more efficient washing.

When washing is carried out with a small amount of water, it is more preferred to provide washing tanks of squeeze rolls and crossover rolls described in JP-A-63-18350, JP-A-62-287252, etc. In order to reduce environmental pollution load which raises a problem in washing with a small amount of water, addition of various oxidizing agents and filtration through filters may be combined with each other.

Moreover, in the method of the present invention, an overflowed solution from a washing or stabilizing bath produced by replenishing water subjected to antifungal treatment to the washing or stabilizing bath depending on processing can also be partly or wholly utilized as a processing solution having fixing ability in the preceding processing step as described in JP-A-60-235133.

Further, in order to prevent foam spots which are liable to occur in washing with a small amount of water, and/or to prevent components of processing agents adhered to the squeeze rolls from being transferred to processed films, water-soluble surfactants or defoaming agents may be added.

Furthermore, for prevention of contamination caused by dyes eluted from the photographic materials, dye adsorbents described in JP-A-63-163456 may be added to washing tanks.

Moreover, the above-mentioned washing processing is followed by stabilization processing in some cases. As an example thereof, baths containing compounds described in JP-A-2-201357, JP-A-2-132435, JP-A-1-102553 and JP-A-46-44446 may be used as final baths for the photographic materials.

Ammonium compounds, compounds of metals such as Bi and Al fluorescent whitening agents, various chelating agents, membrane pH regulators, hardening agents, disinfectants, antifungal agents, alkanolamines or surfactants can also be added to these stabilizing baths. As water used in the washing step or the stabilization step, deionized water and water sterilized with a halogen or ultraviolet germicidal lamp or various oxidizing agents (ozone, hydrogen peroxide, chlorates, etc.), as well as tap water, are preferably used. Washing water containing compounds described in JP-A-4-39652 and JP-A-5-241309 may also be used.

The temperature of the washing or stabilization bath is preferably 0° to 50° C., and the time is preferably 5 seconds to 2 minutes.

The processing solutions used in the present invention are preferably stored by use of wrapping material having low oxygen permeability described in JP-A-61-73147.

The processing solutions used in the present invention may be powdered and solidified. As methods thereof, known methods can be used. However, methods described in JP-A-61-259921, JP-A-4-85533 and JP-A-4-16841 are preferably used, and methods described in JP-A-61-259921 are particularly preferred.

When the replenishment rate is reduced, it is preferred to prevent evaporation and air oxidation of the solution by decreasing the contact area of the processing tank with air. Roller transfer type automatic processors are described in U.S. Pat. Nos. 3,025,779 and 3,545,971, etc., and briefly referred to as roller transfer type processors in this specification. The roller transfer type processor comprises the four steps of development, fixing, washing and drying. It is most preferred that the methods of the present invention also follow these four steps, although not excluding another step (for example, a stop step). Four steps having a stabilization step in place of the washing step may be used.

In water-saving processing or non-piping processing, antifungal means are preferably applied to washing water or stabilizing solutions. It is sometimes more preferred that washing water is passed through a filter member or an activated carbon filter to remove dirt or organic substances existing in water as pretreatment before supply to a washing tank.

Methods which can be used in combination therewith include an ultraviolet irradiation method described in JP-A-60-263939, a method using a magnetic field described in JP-A-60-263940, a method using an ion-exchange resin to obtain pure water described in JP-A-61-131632, a method described in JP-A-4-151143 in which water is circulated through a filter and an adsorbent column while blowing ozone therein, a method using microbial decomposition described in JP-A-4-240636 and methods using microbiocides described in JP-A-62-115154, JP-A-62-153952, JP-A-62-220951 and JP-A-62-209532, which are known as antifungal means.

Further, microbiocides, antifungal agents, surfactants, etc. described in M. W. Reach, "Microbiological Growths in Motion-Picture Processing", *SMPTE Journal*, 85 (1976), R. O. Deegan, "Photo Processing Wash Water Biocides", *J. Imaging Tech.*, 10, No. 6 (1984), JP-A-57-8542, JP-A-57-58143, JP-A-58-105145, JP-A-57-132146, JP-A-58-18631, JP-A-57-97530 and JP-A-57-257244 can also be used in combination as so desired.

Furthermore, isothiazoline compounds and bromochloromethylhydantoin described in R. T. Kreiman, *J. Image. Tech.*, 10, No. 6, 242 (1984), isothiazoline compounds described in *Research Disclosure*, 205, No. 20526 (May, 1981) and ibid., 228, No. 22845 (April, 1983) and compounds described in JP-A-62-209532 can also be used in combination as microbiocides in the washing baths (or the stabilizing baths).

In addition, compounds as described in Hiroshi Horiguchi, *Bohkin Bohbai no Kagaku* (*Chemistry of Bacteria Prevention and Fungus Prevention*), Mitsui Shuppan (1982) and *Bohkin Bohbai Gijutsu Handbook* (*Handbook of Bacteria Prevention and Fungus Prevention*), edited by Nippon Bohkin Bohbai Gakkai, Hakuhohdoh (1986) may be contained.

The photographic materials which have been developed, fixed and washed (or stabilized) are squeezed to remove washing water off, namely allowed to pass through squeeze rolls to dry them. Drying is conducted at 40° to 100° C. The drying time is usually 5 seconds to 3 minutes, and preferably 5 seconds to 2 minutes at 40° to 80° C., although appropriately changed.

When development processing is conducted for 100 seconds or less at dry to dry, it is preferred to apply a roll of rubber material to an outlet roll of a development tank as described in JP-A-63-151943, to agitate a developing solution in a developing solution tank at an extrusion flow rate of 10 m/minute or more as described in JP-A-63-151944, or to agitate more vigorously at least during development processing than during the stand-by condition as described in JP-A-63-264758, in order to prevent uneven development characteristic of rapid processing. Further, for rapid processing, rolls of a fixing tank is more preferably constituted by opposed rolls to increase the fixing speed. The opposed rolls can decrease the number of rolls and minimize the size of the processing tank. That is, it becomes possible to make the automatic processor more compact.

There is no particular limitation on photographic materials to which the methods for processing the photographic materials are applied. Color photographic materials subjected to reversal processing (for example, reversal color films or paper), in addition to general black-and-white photographic materials, can also be used. In particular, the present invention is preferably applied to photographic materials for laser printers and photographic materials for printing of medical images, direct taking X-ray films for medical use, indirect taking X-ray films for medical use, hydrazine nucleating high contrast films, photographic materials for CRT image recording, photographic materials for micro use, general black-and-white negative films and black-and-white photographic paper.

There is no particular limitation on the halogen composition of silver halide emulsions. Silver halides such as silver chloride, silver iodide, silver bromide, silver chlorobromide, silver iodobromide and silver chloroiodobromide are dispersed in hydrophilic colloids.

The silver halide emulsions are prepared by mixing water-soluble silver salts (for example, silver nitrate) and water-soluble halogen salts in the presence of water and hydrophilic colloids by methods well known in the art (for example, the single jet process, the double jet process and the controlled jet process), and subjecting the mixtures to physical ripening and chemical ripening such as gold sensitization and/or sulfur sensitization. There is no particular limitation on the form of silver halide grains used in the present invention, and tabular silver halide grains having a high aspect ratio described in *Research Disclosure*, 22534 (January, 1983), in addition to cubic, octahedral and spherical grains, can be used.

In the case of hydrazine-containing photographic materials, there is no particular limitation on silver halides. However, silver chlorobromide and silver iodochlorobromide having a silver chloride content of 50 mol % or more are preferred. The content of silver iodide is preferably 3 mol % or less, and more preferably 0.5 mol % or less. The form of silver halide grains may be any of cubic, tetradecahedral, octahedral, irregular and tabular, but the cubic form is preferred. The mean grain size of the silver halides is preferably 0.1 μm to 0.7 μm, and more preferably 0.2 to 0.5 μm. The grain size distribution is preferably as narrow as a coefficient of variation represented by {(standard deviation of grain size)/(mean grain size)}×100 of 15% or less, more preferably 10% or less.

The silver halide grain may be composed of uniform layers or different layers in the inside and the surface thereof.

Photographic emulsions can be prepared by use of the methods described in P. Glafkides, *Chimie et Physique Photographique* (Paul Montel, 1967), G. F. Duffin, *Photographic Emulsion Chemistry* (The Focal Press, 1966) and V. L. Zelikman et al., *Making and Coating Photographic Emulsion* (The Focal Press, 1964).

A soluble silver salt and a soluble halogen salt may be reacted with each other by using any of the single jet process, the double jet process and a combination thereof. A process in which grains are formed in the presence of excess silver ions (so-called reverse mixing process) can also be used. As a type of double jet process, there can also be used a process for maintaining the pAg in a liquid phase constant, in which a silver halide is formed, namely the so-called controlled double jet process. Further, it is preferred that so-called solvents for silver halides such as ammonium, thioether and four-substituted thiourea are used to form grains. More preferably, four-substituted thiourea compounds are used, which are described in JP-A-53-82408 and JP-A-55-77737. Preferred examples of the thiourea compounds are tetramethylthiourea and 1,3-dimethyl-2-imidazolidinethione. According to the controlled double jet process and the grain forming process using the solvents for silver halides, silver halide emulsions having a regular crystal form and a narrow grain size distribution can be easily prepared. These processes are useful means for preparing the silver halide emulsions used in the present invention.

Further, in order to homogenize the grain size, it is preferred that grains are allowed to grow rapidly within the range not exceeding the critical degree of saturation by the method of changing the addition rate of silver nitrate and alkali halides depending on the growth speed of grains as described in British Patent 1,535,016, JP-B-48-36890 and JP-B-52-16364, and the method of changing the concentration of aqueous solutions as described in British Patent 4,242,445 and JP-A-55-158124.

In the case of the X-ray photographic materials, the silver amount of the photographic material is desirably 8.0 g/m$^2$ or less as the total on both sides of a support, and more preferably 4.0 g/m$^2$ or less. The photographic materials can have hydrophilic colloidal layers in addition to silver halide emulsion layers if necessary, and surface protective layers are preferably provided in accordance with known methods. The amount of gelatin on the sides having the hydrophilic colloidal layers containing the emulsion layers is preferably within the range from 2.0 g/m$^2$ to less than 5.0 g/m$^2$, and particularly preferably established within the range from 2.5 g/m$^2$ to less than 4.0 g/m$^2$. The melting time of the photographic materials is preferably established to 20 minutes to 100 minutes. This melting time is measured according to the method described in JP-A-63-221341.

A halogen surfactant photographic material is one having at least one halogen surfactant emulsion layer on a support. In the case of the direct X-ray photographic material for medical use, it is preferred that the photographic material has at least one halogen surfactant emulsion layer on each side of a support, as described in JP-A-58-127921, JP-A-59-90841, JP-A-58-111934 and JP-A-61-201235.

The photographic materials can additionally have intermediate layers, filter layers, antihalation layers, etc. if necessary.

The silver amount of the photographic materials is preferably 0.5 g/m$^2$ to 5 g/m$^2$ (on one side), and more preferably 1 g/m$^2$ to 3 g/m$^2$ (on one side).

As rapid processing suitability, it is preferred that the amount does not exceed 5 g/m$^2$. Further, in order to obtain a definite image density and contrast, the amount is preferably 0.5 g/m$^2$ or more.

For emulsion grains used in the X-ray photographic materials, silver halide grains in the emulsions may have regular crystal forms such as cubic and octahedral, or irregular crystal forms such as spherical, tabular and potato-like, or the grains may be composed of mixtures of grains having various crystal forms.

The composition of the silver halide grains may be any of silver iodobromide, silver bromide, silver iodochlorobromide, silver chlorobromide, silver iodochloride and silver chloride. Silver iodobromide having a silver iodide content of 0.6 mol % or less, and silver iodochlorobromide and silver chlorobromide having a silver chloride content of 20 mol % to less than 100 mol %, particularly 50 mol % to less than 99 mol % are desirable, from the viewpoint of high sensitivity and excellent rapid processing performance.

The use of monodisperse emulsions is a preferred embodiment. Methods for preparing the monodisperse emulsions are well known, and techniques described, for example, in *J. Photo. Sci.*, 12, 242–251 (1963), JP-B-48-36890, JP-B-52-16364, JP-A-55-142329, JP-A-57-179835, etc. can be appropriately utilized. Further, the emulsions may be core/shell type silver halide emulsions. The core/shell type silver halide emulsions are well known by JP-A-54-48521, etc.

The use of tabular grains is a preferred embodiment. For the tabular grains, *Research Disclosure*, 225, Item 22534, 20–58 (January, 1983), JP-A-58-127921, JP-A-58-113926, JP-A-58-113927, JP-A-58-113928 and U.S. Pat. No. 4,439,520 can be referred to.

The diameter of a circle equivalent to a projected area of the tabular emulsion is preferably 0.3 to 2.0 μm, and particularly 0.5 to 1.2 μm. The thickness of the grain is preferably 0.05 to 0.3 μm, and particularly 0.1 to 0.25 μm, and the aspect ratio is preferably 3 to less than 20, and particularly 5 to less than 12.

Of the tabular grains, monodisperse tabular grains are particularly useful grains. The details of the structure and the manufacturing method of the monodisperse tabular grains in the present invention follow the descriptions or JP-A-63-151618 and JP-A-1-158426.

As the silver halide emulsions used in the X-ray photographic materials, tabular silver chlorobromide and/or silver chloride emulsions are preferred. With respect to the tabular silver chlorobromide and/or silver chloride emulsions, emulsions mainly having (111) faces as crystal habit and emulsions mainly having (100) faces are known. The (111) tabular silver chlorobromide emulsions described in JP-B-64-8325, JP-B-64-8326, JP-A-62-111936 and JP-A-62-163046 are well known.

On the other hand, the (100) tabular silver chlorobromide emulsions are described in JP-A-51-88017, JP-B-64-8323, European Patent 0,534,395A1, etc. However, techniques described in JP-A-7-120857 and JP-A-7-128767 are particularly desirable because of narrow grain size distribution and high sensitivity, and a combination of the (100) tabular silver chloride grains and ascorbic acid development processing as described in Japanese Patent Application No. 5-316677 is also a preferred embodiment.

Use of the tabular silver halide emulsions can further increase the stability of photographic characteristics in running processing according to the present invention. Furthermore, the amount of silver applied can be decreased, so that the loads of the fixing step and the drying step are particularly reduced. Also from this point, rapid processing becomes possible.

The tabular silver halide emulsions are described in Cugnac and Chateau, "Evolution of the Morphology of Silver Bromide Crystals during Physical Ripening", *Science et Industries Photographiques*, 33, No. 2, 121–125 (1962), Duffin, *Photographic Emulsion Chemistry*, pages 66–72 (Focal Press, New York, 1966) and A. P. H. Tribvlli and W. F. Smith, *Photographic Journal*, 80, 285 (1940), and they can be easily prepared by referring to the methods described in JP-A-58-127921, JP-A-58-113927 and JP-A-58-113928.

Further, they are obtained by forming seed crystals containing 40% by weight of tabular grains in an atmosphere of a relatively low pBr value of pBr 1.3 or less, and allowing the seed crystals to grow while concurrently adding silver and halogen solutions with keeping the pBr value to a similar degree.

It is desirable that the silver and halogen solutions are added in such a manner that a new crystalline nucleus is not developed during the course of this grain growth.

The size of the tabular silver halide grains can be adjusted by temperature control, selection of the kind and amount of solvent, and controlling the addition rate of a silver salt and a halide used in grain growth.

The silver halide grain used in the silver halide photographic material preferably contains at least one metal selected from the group consisting of rhodium, rhenium, ruthenium, osmium and iridium in order to achieve high contrast and low fog. The content thereof is preferably within the range of $1\times10^{-9}$ mol to $1\times10^{-5}$ mol per mol of silver, and more preferably within the range of $1\times10^{-8}$ mol to $1\times10^{-6}$ mol.

These metals may be used as a combination of two or more of them. The silver halide grains can contain these metals homogeneously or with a distribution in a grain as described in JP-A-63-29603, JP-A-2-306236, JP-A-3-167545, JP-A-4-76534 and JP-A-6-110146.

As rhodium compounds, water-soluble rhodium compounds can be used. Examples thereof include rhodium (III) halide compounds or rhodium complex salts having halogens, amines, oxalato or the like as ligands, for example, hexachlororhodium (III) complex salts, hexabromorhodium (III) complex salts, hexaaminerhodium (III) complex salts and trioxalatorhodium (III) complex salts. These rhodium compounds are dissolved in water or appropriate solvents to use them. In order to stabilize the solution of the rhodium compound, a method generally frequently used, that is, the method of adding an aqueous solution of a hydrogen halide (for example, hydrochloric acid, hydrobromic acid, hydrofluoric acid or the like) or an alkali halide (for example, KCl, NaCl, KBr, NaBr or the like) can be used. Instead of use of the water-soluble rhodium, it is also possible to add and dissolve other silver halide grains previously doped with rhodium in preparing the silver halide.

Addition of these compounds can be appropriately conducted in preparing the silver halide emulsion grains and in each step prior to coating of the emulsions. In particular, the compounds are preferably added in forming the emulsions to incorporate them into the silver halide grains.

Rhenium, ruthenium and osmium are added in the form of water-soluble complex salts described in JP-A-63-2042, JP-A-1-285941, JP-A-2-20852, JP-A-2-20855, etc. Particularly preferred examples thereof include six-coordinate complexes represented by the following formula:

$$[ML_6]^{n}$$

wherein M represents Ru, Re or Os, and n represents 0, 1, 2, 3 or 4.

In this case, counter ions have no importance, and ammonium or alkali metal ions are used.

Further, preferred examples of the ligands include halide ligands, cyanide ligands, cyanate ligands, nitrosyl ligands and thionitrosyl ligands. Examples of the complexes used in the present invention are shown below, but the present invention is not limited thereto.

| | | |
|---|---|---|
| $[ReCl_6]^{-3}$ | $[ReBr_6]^{-3}$ | $[ReCl_5(NO)]^{-2}$ |
| $[Re(NS)Br_5]^{-2}$ | $[Re(NO)(CN)_5]^{-2}$ | $[ReO_2(CN)_4]^{-3}$ |
| $[RuCl_6]^{-3}$ | $[RuCl_4(H_2O)_2]^{-2}$ | $[RuCl_5(NO)]^{-2}$ |
| $[RuBr_5(NS)]^{-2}$ | $[Ru(CN)_6]^{-4}$ | $[Ru(CO)_3Cl_3]^{-2}$ |
| $[Ru(CO)Cl_5]^{-2}$ | $[Ru(CO)Br_5]^{-2}$ | |
| $[OsCl_6]^{-3}$ | $[OsCl_5(NO)]^{-2}$ | $[Os(NO)(CN)_5]^{-2}$ |
| $[Os(NS)Br_5]^{-2}$ | $[Os(CN)_6]^{-4}$ | $[OsO_2(CN)_4]^{-4}$ |

Addition of these compounds can be appropriately conducted in preparing the silver halide emulsion grains and in each step prior to coating of the emulsions. In particular, the compounds are preferably added in forming the emulsions to incorporate them into the silver halide grains.

In order to add these compounds during formation of the silver halide grains to incorporate them into the silver halide grains, there are the method of adding an aqueous solution in which the compound is dissolved together with a metal complex powder or NaCl and KCl to a solution of a water-soluble salt or a water-soluble halide during formation of the grains, the method of adding the compound as the third solution when the silver salt and halide solutions are concurrently mixed to prepare the silver halide grains by a three-liquid concurrent mixing process, and the method of putting an aqueous solution of a required amount of a metal complex into a reaction vessel during formation of the grains. In particular, the method of adding the aqueous solution in which the compound is dissolved together with the powder or NaCl and KCl to the solution of the water-soluble halide is preferred.

In order to add the compound to surfaces of the grains, the aqueous solution of a required amount of the metal complex can also be put into the reaction vessel just after formation of the grains, during or at the end of physical ripening, or in chemical ripening.

As the iridium compounds, various compounds can be used. Examples thereof include hexachloroiridium, hexaamineiridium, trioxalatoiridium and hexacyanoiridium.

These iridium compounds are dissolved in water or appropriate solvents to use them. In order to stabilize the solution of the iridium compound, a method generally frequently used, that is, the method of adding an aqueous solution of a hydrogen halide (for example, hydrochloric acid, hydrobromic acid, hydrofluoric acid or the like) or an alkali halide (for example, KCl, NaCl, KBr, NaBr or the like) can be used. Instead of use of the water-soluble iridium, it is also possible to add and dissolve other silver halide grains previously doped with iridium in preparing the silver halide.

The silver halide grains may be doped with other heavy metal salts. In particular, doping with Fe salts such as $K_4[Fe(CN)_6]$ is advantageously carried out.

The silver halide grains may contain metal atoms such as cobalt, nickel, palladium, platinum, gold, thallium, copper and lead. The above-mentioned metals are preferably contained in an amount of $1\times10^{-9}$ to $1\times10^{-4}$ mol per mol of silver halide. When the above-mentioned metals are added, they can be added in the form of single salts, double salts or complex salts in preparing the grains.

The silver halide emulsions are preferably subjected to chemical sensitization, and known methods such as sulfur sensitization, selenium sensitization, tellurium sensitization, reduction sensitization and noble metal sensitization can be used alone or in combination. When they are used in combination, for example, sulfur sensitization and gold sensitization; sulfur sensitization, selenium sensitization and gold sensitization; and sulfur sensitization, tellurium sensitization and gold sensitization are preferred.

The sulfur sensitization is usually conducted by adding a sulfur sensitizer and stirring an emulsion at a high temperature of 40° C. or more for a definite period of time. As the sulfur sensitizers, known compounds can be used. Examples thereof include various sulfur compounds such as thiosulfates, thiourea compounds, thiazole compounds and rhodanine compounds, as well as sulfur compounds contained in gelatin. Preferred sulfur compounds are thiosulfates and thiourea compounds. Although the amount of the sulfur sensitizers added varies depending on various conditions such as the pH in chemical ripening, the temperature and the size of silver halide grains, it is $10^{-7}$ to $10^{-2}$ mol per mol of silver halide, and more preferably $10^{-5}$ to $10^{-3}$ mol.

As selenium sensitizers, known selenium compounds can be used. That is, the selenium sensitization is usually conducted by adding an unstable type and/or non-unstable type selenium compound and stirring an emulsion at a high temperature, preferably at 40° C. or more, for a definite period of time. As the unstable type selenium compounds, compounds described in JP-B-44-15748, JP-B-43-13489, JP-A-4-25832, JP-A-4-109240 and JP-A-4-324855, etc. can be used. In particular, compounds represented by general formulas (VIII) and (IX) in JP-A-4-324855 are preferably used.

Tellurium sensitizers are compounds producing silver telluride presumed to form a sensitizing nucleus in the surface or the inside of a silver halide grain. The forming rate of silver telluride in the silver halide emulsion can be tested by the method described in JP-A-5-313284.

Specifically, there can be used compounds described in U.S. Pat. Nos. 1,623,499, 3,320,069 and 3,772,031, British Patents 235,211, 1,121,496, 1,295,462 and 1,396,696, Canadian Patent 800,958, JP-A-4-204640, JP-A-4-271341, JP-A-4-333043 and JP-A-5-303157, *J. Chem. Soc. Chem. Commnun.*, 635 (1980), ibid., 1102 (1979), ibid., 645 (1979), *J. Chem. Soc. Perkin, Trans.*, 1, 2191 (1980), *The Chemistry of Organic Selenium and Tellurium Compounds*, vol.1, edited by S. Pa tai (1986) and ibid. vol. 2 (1987). In particular, compounds represented by general formulas (II), (III) and (IV) in JP-A-5-313284 are preferably used.

Although the amount of the selenium and tellurium sensitizers added varies depending on silver halide grains used, chemical ripening conditions, etc., it is generally $10^{-8}$ to $10^{-2}$ mol per mol of silver halide, and preferably about $10^{-7}$ to $10^{-3}$ mol. There is no particular limitation on the chemical ripening conditions of the present invention. However, the pH is 5 to 8, the pAg is 6 to 11 and preferably 7 to 10, and the temperature is 40° to 95° C. and preferably 45° to 85° C.

Noble metal sensitizers include gold, platinum and palladium, and particularly gold sensitization is preferred. Examples of gold sensitizers used in the present invention include chloroauric acid, potassium chloroaurate, potassium aurithiocyanate and gold sulfide. They can be used in an amount of about $10^{-7}$ to $10^{-2}$ mol/mol of silver halide.

In the course of formation of the silver halide grains and physical ripening, cadmium salts, sulfites, lead salts, thallium salts, etc. may be allowed to coexist with the silver halide emulsions.

In the present invention, the reduction sensitization can be used.

As reduction sensitizers, stannous salts, amines, formamidinesulfinic acid, silane compounds, etc. can be used.

Thiosulfonic acid compounds may be added to the silver halide emulsions by the method shown in EP-293,917.

The silver halide emulsions in the photographic materials may be used alone or in combination (for example, emulsions different in mean grain size, emulsions different in halogen composition, emulsions different in crystal habit, and emulsions different in chemical ripening conditions).

The silver halide emulsions may be multidisperse emulsions, but may be monodisperse emulsions uniform in grain size distribution. In particular, monodisperse emulsions having a coefficient of dispersion of 20% or less are preferably used in photographic materials for printing, the coefficient indicating grain size distribution. The monodisperse emulsion used herein means a silver halide emulsion having a grain size distribution in which the coefficient of variation is 20% or less, particularly preferably 15% or less, wherein the coefficient of variation is defined by the coefficient of variation (%)={(standard deviation of grain size)/(mean grain size)}×100.

The silver halide grain may be composed of uniform phases or different phases in the inside and the surface thereof. Two or more kinds of silver halide emulsions separately prepared may be mixed for use.

The silver halide grain may be either a grain in which a latent image is mainly formed on a surface of the grain or a grain in which a latent image is mainly formed in the inside of the grain. Further, the grain may be a grain whose surface is previously fogged.

The swelling percentage used in the present invention can be determined by (a) incubating the above-mentioned photographic material at 38° C. at a relative humidity of 50% for 3 days, (b) measuring the thickness of a hydrophilic colloidal layer, (c) immersing the photographic material in distilled water at 21° C. for 3 minutes, and (d) measuring the percentage of changes in layer thickness, comparing with the thickness of the hydrophilic colloidal layer measured in step (b).

The swelling percentage of the hydrophilic colloidal layer containing at least one silver halide emulsion layer is preferably 300% or less, and more preferably 150% to 250%, for the X-ray photographic material, and preferably 250% or less, and more preferably 100% to 200%, for a photographic material for graphic arts.

Such rapid processing and simplification of processing can be better achieved by further reducing the swelling percentage.

On the other hand, a reduction in swelling percentage results in decreased speed of development, fixing, washing, etc. It is therefore unfavorable to reduce the swelling percentage more than it needs.

As hardening agents which can be used, there are known, for example, aldehyde compounds, active halogen-containing compounds described in U.S. Pat. No. 3,288,775, compounds having reactive ethylenic unsaturated groups described in U.S. Pat. No. 3,635,718, epoxy compounds described in U.S. Pat. No. 3,091,537, and organic compounds such as halogenocarboxyaldehydes such as mucochloric acid. Of these, vinylsulfone hardening agents are preferred. Further, polymer hardening agents can also be preferably used.

As the polymer hardening agents, polymers having active vinyl groups or precursor groups thereof are preferred. Of these, polymers in which active vinyl groups or precursor groups thereof are linked by long spacers to main polymer chains as described in JP-A-56-142524 are particularly preferred. The amount of these hardening agents added to achieve the swelling percentage of the present invention varies depending on the kind of hardening agent used and the gelatin species.

It is preferred that the silver halide grains are spectrally sensitized by use of sensitizing dyes. The sensitizing dyes used include cyanine dyes, merocyanine dyes, complex cyanine dyes, complex merocyanine dyes, holopolar cyanine dyes, hemicyanine dyes, styryl dyes and hemioxanol dyes. Particularly useful dyes are dyes belonging to the cyanine dyes, the merocyanine dyes and the complex merocyanine dyes.

Any nuclei usually utilized in cyanine dyes as basic heterocyclic ring nuclei can be applied to these dyes. That is, there can be applied pyrroline, oxazoline, thiazoline, pyrrole, oxazole, thiazole, selenazole, imidazole, tetrazole and pyridine nuclei, nuclei in which alicyclic hydrocarbon rings are fused together with these nuclei, and nuclei in which aromatic hydrocarbon rings are fused together with these nuclei, namely, indolenine, benzoindolenine, indole, benzoxazole, naphthoxazole, benzothiazole, naphthothiazole, benzoselenazole and benzimidazole nuclei. These nuclei may be substituted on carbon atoms.

To the merocyanine dyes and the complex merocyanine dyes, 5- and 6-membered heterocyclic ring nuclei such as pyrazoline-5-one, thiohydantoin, 2-thiooxazolidine-2,4-dione, thiazolidine-2,4-dione, rhodanine and thiobarubituric acid nuclei can be applied as nuclei having the keto-methylene structure.

Specifically, compounds described in *Research Disclosure,* 170, RD-17643, page 23, (December, 1978), U.S. Pat. Nos. 4,425,425 and 4,425,426 can be used. Specifically, the following compounds can be used:

5,5'-Dichloro-3,3'-diethylthiacyanine bromide 5,5'-Dichloro-3,3'-di(4-sulfobutyl)thiacyanine Na salt 5-Methoxy-4,5-benzo-3,3'-di(3-sulfopropyl)thiacyanine Na salt 5,5'-Dichloro-3,3'-diethylselenacyanine iodide 5,5'-Dichloro-9-ethyl-3,3'-di(3-sulfopropyl)thiacarbocyanine pyridinium salt Anhydro-5,5'-dichloro-9-ethyl-3-(4-sulfobutyl)-3-ethyl hydroxide 1,1-Diethyl-2,2'-cyanine bromide 1,1-Dipentyl-2,2'-cyanine perchrolic acid 9-Methyl-3,3'-di(4-sulfobutyl)-thiacarbocyanine pyridinium salt 5,5'-Diphenyl-9-ethyl-3,3'-di(2-sulfoethyl) oxacarbocyanine Na salt 5-Chloro-5'-phenyl-9-ethyl-3-(3-sulfopropyl)-3'-(2-sulfoethyl)oxacarbocyanine Na salt 5,5'-Dichloro-9-ethyl-3,3'-di(3-sulfopropyl) oxacarbocyanine Na salt 5,5'-Dichloro-6,6'-dichloro-1,1'-diethyl-3,3'-di(3-sulfopropyl)imidacarbocyanine Na salt 5,5'-Diphenyl-9-ethyl-3,3'-di(3-sulfopropyl)thiacarbocyanine Na salt The time when the sensitizing dyes are added to the emulsions is generally before application of the emulsions on appropriate supports, but may be in the chemical ripening step or in the silver halide grain forming step.

Useful dyes, combinations of dyes exhibiting supersensitization and substances exhibiting supersensitization are described in *Research Disclosure,* 176, 17643, page 23, section IV-J (December, 1978), or JP-B-49-25500, JP-B-43-4933, JP-A-59-19032 and JP-A-59-192242 described above.

In order to allow the sensitizing dye to be contained in the silver halide emulsion, it may be directly dispersed in the emulsion, or dissolved in a single solvent such as water, methanol, ethanol, propanol, acetone, methyl cellosolve, 2,2,3,3-tetrafluoropropanol, 2,2,2-trifluoroethanol, 3-methoxy-1-propanol, 3-methoxy-1-butanol, 1-methoxy-2-propanol or N,N-dimethylformamide, or in a mixed solvent thereof to add to the emulsion.

Further, there can also be used the method of dissolving a dye in a volatile organic solvent, dispersing the solution in water or a hydrophilic colloid, and adding the dispersion to an emulsion, as described in U.S. Pat. No. 3,469,987; the method of dispersing a water-insoluble dye in a water-soluble solvent without dissolving it, and adding the dispersion to an emulsion, as described in JP-B-46-24185; the method of dissolving a dye in an acid and adding the solution to an emulsion, or allowing an acid or a base to coexist to form an aqueous solution and adding it to an emulsion, as described in JP-B-44-23389, JP-B-44-27555 and JP-B-57-22091; the method of allowing a surfactant to coexist to form an aqueous solution or a colloidal dispersion, and adding it to an emulsion, as described in U.S. Pat. Nos. 3,822,135 and 4,006,026; the method of directly dispersing a dye in a hydrophilic colloid, and adding the dispersion to an emulsion, as described in JP-A-53-102733 and JP-A-58-105141; and the method of dissolving a dye using a compound capable of shifting a dye into a red (longer wavelength) region, and adding the solution to an emulsion, as described in JP-A-51-74624.

Further, ultrasonic waves can be used for dissolution.

The time when the sensitizing dyes are added to the silver halide emulsions may be during any steps of emulsion preparation which have hitherto been recognized to be useful. For example, they may be added during the silver halide grain forming step or/and before salt removal, during the salt removal step and/or at the time from before salt removal to before initiation of chemical ripening, as described in U.S. Pat. Nos. 2,735,766, 3,628,960, 4,183,756 and 4,225,666, JP-A-58-184142, JP-A-60-196749, etc., or just before chemical ripening or during the step, any time and steps before application of the emulsions after chemical ripening, as described in JP-A-58-113920, etc. Further, as disclosed in U.S. Pat. No. 4,225,666, JP-A-58-7629, etc., the same compound may be added alone or in combination with a compound different in structure, and the compound may be added in parts, for example, during the grain forming step and the chemical ripening step or after completion of chemical ripening, or before chemical ripening or the step and after the completion. The compounds may be added, changing the compounds added in parts and the kind of combination of the compounds.

The amount of the sensitizing dyes added is preferably $4\times10^{-8}$ to $8\times10^{-2}$ mol per mol of silver halide, though it varies depending on the form and size of silver halide grains.

Plasticizers, for example, polymer latexes such as alkyl acrylate latexes and polyols such as trimethylol propane, can be added to the emulsion layers of the photographic materials to improve pressure characteristics.

The photographic materials may be designed so as to exhibit superhigh contrast photographic characteristics using hydrazine nucleating agents. This system and hydrazine nucleating agents to be used are described in the following literatures. This system is suitably used particularly for graphic arts. *Research Disclosure,* Item 23516, p-346 (November, 1983) and literatures cited therein, U.S. Pat. Nos. 4,080,207, 4,269,929, 4,276,364, 4,278,748, 4,385,108, 4,459,347, 4,478,928, 4,560,638, 4,686,167, 4,912,016, 4,988,604, 4,994,365, 5,041,355 and 5,104,760, British Patent 2,011,391B, European Patents 217,310, 301,799 and 356,898, JP-A-60-179734, JP-A-61-170733, JP-A-61-270744, JP-A-62-178246, JP-A-62-270948, JP-A-63-29751, JP-A-63-32538, JP-A-63-104047, JP-A-63-121838, JP-A-63-129337, JP-A-63-223744, JP-A-63-234244, JP-A-63-234245, JP-A-63-234246, JP-A-63-294552, JP-A-63-306438, JP-A-64-10233, JP-A-64-90439, JP-A-1-100530, JP-A-1-105941, JP-A-1-105943, JP-A-1-276128, JP-A-1-280747, JP-A-1-283548, JP-A-1-283549, JP-A-1-285940, JP-A-2-2541, JP-A-2-139538, JP-A-2-177057, JP-A-2-196234, JP-A-2-196235, JP-A-2-198440, JP-A-2-198441, JP-A-2-198442, JP-A-2-220042, JP-A-2-221953, JP-A-2-221954, JP-A-2-230233, JP-A-2-285243, JP-A-2-285343, JP-A-2-289843, JP-A-2-302750, JP-A-2-304550, JP-A-3-37642, JP-A-3-54549, JP-A-3-125134, JP-A-3-184039, JP-A-3-240036, JP-A-3-240037, JP-A-3-259240, JP-A-3-280038, JP-A-3-282536, JP-A-4-51143, JP-A-4-56842, JP-A-4-84134, JP-A-4-96053, JP-A-4-216544, JP-A-5-45761, JP-A-5-45762, JP-A-5-45763, JP-A-5-45764, JP-A-5-45765, JP-A-5 -94925, etc.

When the hydrazine nucleating agents are added to the photographic materials, they are preferably added to the silver halide emulsion layers. However, they may be added to light-insensitive hydrophilic colloidal layers (for example, protective layers, intermediate layers, filter layers, antihalation layers, etc.) other than the silver halide emulsion layers. The amount of the hydrazine nucleating agents added is preferably within the range of $1\times10^{-6}$ mol to $5\times10^{-2}$ mol per mol of silver halide, and particularly preferably with in the range of $1\times10^{-5}$ mol to $2\times10^{-2}$ mol.

The hydrazine compounds can be dissolved in appropriate solvents such as alcohols (methanol, ethanol, propanol and fluorinated alcohols), ketones (acetone and methyl ethyl ketone), dimethylformamide, dimethyl sulfoxide and methyl cellosolve to use them.

Further, they can also be dissolved using oil such as dibutyl phthalate, tricresyl phosphate, glyceryl triacetate or diethyl phthalate, and an auxiliary solvent such as ethyl acetate or cyclohexanone by the emulsifying dispersion methods already well known to mechanically form emulsified dispersions for use. Powdered hydrazine compounds can also be dispersed in water by a ball mill, a colloid mill or ultrasonic waves according to methods known as the solid dispersion methods to use them.

In the silver halide photographic materials, nucleating accelerators such as amine derivatives, onium salts, disulfide derivatives, hydroxylamine derivatives, acetylene derivatives and urea derivatives are preferably added to the silver halide emulsion layers or other hydrophilic colloidal layers.

The nucleating accelerators include amine derivatives, onium salts, disulfide derivatives or hydroxymethyl derivatives.

The amine derivatives include, for example, compounds described in JP-A-60-140340, JP-A-62-50829, JP-A-62-222241, JP-A-62-250439, JP-A-62-280733, JP-A-63-124045, JP-A-63-133145, JP-A-63-286840, etc. More preferred examples of the amine derivatives include compounds having groups adsorbed by silver halides described in JP-A-63-124045, JP-A-63-133145, JP-A-63-286840, etc., compounds having a total carbon atom number of 20 or more described in JP-A-62-222241, amine compounds having ethylene groups described in U.S. Pat. No. 4,975,354, EP-A-458706 and compounds described in JP-A-62-50829.

As the onium salts, pyridinium salts, ammonium salts or phosphonium sats are preferred. Preferred examples of the pyridinium salts include compounds described in JP-A-62-242534. Further, preferred examples of the ammonium salts include compounds described in JP-A-62-250439, JP-A-62-280733, etc. Furthermore, preferred examples of the phosphonium salts include compounds described in JP-A-61-167939, JP-A-62-280733, etc.

The disulfide derivatives include, for example, compounds described in JP-A-61-198147.

The hydroxymethyl derivatives include, for example, compounds described in U.S. Pat. Nos. 4,698,956 and 4,777,118, EP 231,850, JP-A-62-50829, etc., and more preferably diarylmethacrinol derivatives.

The acetylene derivatives include, for example, compounds described in JP-A-3-168735, JP-A-2-271351, etc.

The urea derivatives include, for example, compounds described in JP-A-3-168736.

Although the optimum amount of the nucleating accelerators added varies depending on the kind thereof, they are desirably used within the range of $1.0\times10^{-2}$ mol to $1.0\times10^{2}$ mol per mol of hydrazine compound, preferably within the range of $1.0\times10^{-1}$ mol to $5.0\times10$ mol.

These compounds can be dissolved in appropriate water-miscible organic solvents such as alcohols (methanol, ethanol, propanol and fluorinated alcohols), ketones (acetone and methyl ethyl ketone), dimethylformamide, dimethyl sulfoxide and methyl cellosolve to use them.

Further, they can also be dissolved using oil such as dibutyl phthalate, tricresyl phosphate, glyceryl triacetate or diethyl phthalate, and an auxiliary solvent such as ethyl acetate or cyclohexanone by the emulsifying dispersion methods already well known to mechanically form emulsified dispersions for use. Powdered compounds can also be dispersed in water by a ball mill, a colloid mill or ultrasonic waves according to methods known as the solid dispersion methods to use them.

As development accelerators suitable for use in this superhigh contrast system or accelerators for nucleation infectious development, various compounds containing N or S atoms, as well as compounds disclosed in JP-A-53-77616, JP-A-54-37732, JP-A-53-137133, JP-A-60-140340, JP-A-60-14959, etc., are effective.

Although the optimum amount of these accelerators added varies depending on the kind of compound, they are desirably used within the range of $1.0\times10^{-3}$ to 0.5 g/m$^2$, preferably within the range of $5.0\times10^{-3}$ to 0.1 g/m$^2$.

Further, in the superhigh contrast system, redox compounds releasing development inhibitors can be used in combination. As the redox compounds, there can be used compounds described in JP-A-2-293736, JP-A-2-308239, JP-A-1-154060, JP-A-1-205885, etc. They are preferably used in an amount ranging from $1\times10^{-6}$ to $5\times10^{-2}$ mol per mol of silver halide, particularly ranging from $1\times10^{-5}$ to $1\times10^{-2}$ mol.

Photographic emulsion layers or other hydrophilic colloidal layers of the photographic materials may contain various surfactants for the various purposes of coating aids, static charge prevention, improvement in sliding properties, emulsified dispersion, adhesion prevention, improvement in photographic characteristics (for example, development acceleration, hard gradation enhancement and sensitization), etc.

Examples of such surfactants include nonionic surfactants such as saponin (steroid series), alkylene oxide derivatives (for example, polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or amides and polyethylene oxide adducts of silicones), glycidol derivatives (for example, alkenylsuccinic acid polyglycerides and alkylphenol polyglycerides), fatty acid esters of polyhydric alcohols and alkyl esters of saccharides; anionic surfactants containing acid groups such as carboxyl, sulfo, phospho, sulfuric ester and phosphoric ester groups, such as alkylcarbonates, alkylsulfonates, alkylbenezenesulfonates, alkylnaphthalenesulfonates, alkylsulfuric esters, alkylphosphoric esters, N-acyl-N-alkyltaurines, sulfosuccinic esters, sulfoalkyl polyoxyethylene alkylphenyl ethers and polyoxyethylene alkylphosphoric esters; amphoteric surfactants such as amino acids, aminoalkylsulfonic acids, aminoalkylsulfuric or phosphoric esters, alkylbetaines and amino oxides; and cationic surfactants such as alkylamine salts, aliphatic or aromatic quaternary ammonium salts, heterocyclic quaternary ammonium salts such as pyridinium and imidazolium, and phosphonium or sulfonium salts containing aliphatic or heterocyclic rings.

Gelatin is advantageously used as a binder or a protective colloid for photographic emulsions, but other hydrophilic colloids can also be used. Examples thereof include gelatin derivatives, graft polymers of gelatin and other polymers, proteins such as albumin and casein, cellulose derivatives such as hydroxyethyl cellulose, carboxymethyl cellulose and cellulose sulfate, saccharide derivatives such as sodium alginate and starch derivatives, and many kinds of synthetic hydrophilic polymer substances such as homopolymers or copolymers of polyvinyl alcohol, polyvinyl alcohol partial acetal, poly-N-vinylpyrrolidone, polyacrylic acid, polymethacrylic acid, polyacrylamide, polyvinylimidazole and polyvinylpyrazole.

As gelatin, acid-treated gelatin, as well as lime-treated gelatin, may be used, and hydrolyzed products of gelatin and enzyme-decomposed products of gelatin can also be used.

It is preferred particularly in the X-ray photographic materials that the emulsion layers and other hydrophilic colloidal layers contain organic materials which flow out in the development step. When the material which flows out is gelatin, gelatin species not related to the crosslinking reaction with hardening agents are preferred. For example, acetylated gelatin and phthalated gelatin correspond thereto, and gelatin having a lower molecular weight is preferred. On the other hand, as the polymer materials other than gelatin, polyacrylamide as described in U.S. Pat. No. 3,271,158 or hydrophilic polymers such as polyvinyl alcohol and polyvinylpyrrolidone can be effectively used, and saccharides such as dextran, saccharose and pullulan are also effective. Of these, polyacrylamide and dextran are preferred, and polyacrylamide is a particularly preferred material. The average molecular weight of these materials is preferably 20,000 or less, and more preferably 10,000 or less. The flow-out amount in processing is effectively 10% to 50% based on the total weight of the organic materials applied other than the silver halide grains, and it is preferred that 15% to 30% disappears.

The organic material which flows out in processing may be contained in either the emulsion layers or a surface protective layer. When the total amount of the organic materials applied is the same, addition to both the emulsion layers and the surface protective layer is preferred to addition to only the emulsion layers, and addition to only the surface protective layer is more preferred. In the photographic materials having emulsion layer of multilayer structure, it is preferred that more organic material is contained in an emulsion layer closer to the surface protective layer provided that the total amount of the organic materials applied is the same.

Antistatic agents which can be preferably used include fluorine-containing surfactants or polymers described in JP-A-62-109044 and JP-A-62-215272, nonionic surfactants described in JP-A-60-76742, JP-A-60-80846, JP-A-60-80848, JP-A-60-80839, JP-A-60-76741, JP-A-58-208743, JP-A-62-172343, JP-A-62-173459, JP-A-62-215272, etc., and conductive polymers or latexes (nonionic, anionic, cationic and amphoteric) described in JP-A-57-204540 and JP-A-62-215272. As inorganic antistatic agents, conductive tin oxide, zinc oxide or complex oxides in which these metal oxides are doped with antimony, etc. described in JP-A-57-118242, etc. can be preferably used.

As matting agents, there can be used a homopolymer of polymethyl methacrylate or a copolymer of methyl methacrylate and methacrylic acid as described in U.S. Pat. Nos. 2,992,101, 2,701,245, 4,142,894 and 4,396,706, organic compounds such as starch, and finely divided grains of inorganic compounds such as silica, titanium dioxide, sulfuric acid, strontium and barium. The grain size is preferably 1.0 to 10 μm, and particularly preferably 2 to 5 μm.

In the silver halide photographic materials, dyes or colloidal silver may be added to photographic emulsion layers or other layers for the purpose of absorbing light within the particular wavelength range, namely preventing halation or irradiation, or providing filter layers to control spectral composition of light to be incident on the photographic emulsion layers. In duplitized films such as direct X-ray films for medical use, layers for crossover cut may be provided beneath the emulsion layers. Such dyes include oxonol dyes having pyrazolone nuclei or barbituric acid nuclei, azo dyes, azomethine dyes, anthraquinone dyes, arylidene dyes, styryl dyes, triarylmethane dyes, merocyanine dyes and cyanine dyes. The dyes are described in more detail.

Examples of such dyes include oxonol dyes having pyrazolone nuclei, barbitur nuclei or barbituric acid nuclei described in British Patents 506,385, 1,177,429, 1,131,884, 1,338,799, 1,385,371, 1,467,214, 1,438,102 and 1,553,516, JP-A-48-85130, JP-A-49-114420, JP-A-52-117123, JP-A-55-161233, JP-A-59-111640, JP-B-39-22069, JP-B-43-13168, JP-B-62-273527, U.S. Pat. Nos. 3,247,127, 3,469,985, 4,078,933, etc., other oxonol dyes described in U.S. Pat. Nos. 2,533,472 and 3,379,533, British Patent 1,278,621, JP-A-l-134447, JP-A-1-183652, etc., azo dyes described in British Patents 575,691, 680,631, 599,623, 786,907, 907,125 and 1,045,609, U.S. Pat. No. 4,255,326, JP-A-59-211043, etc., azomethine dyes described in JP-A-50-100116, JP-A-54-118247, British Patents 2,014,598 and 750,031, etc., anthraquinone dyes described in U.S. Pat. No. 2,865,752, arylidene dyes described in U.S. Pat. Nos. 2,538,009, 2,688,541 and 2,538,008, British Patents 584,609 and 1,210,252, JP-A-50-40625, JP-A-51-3623, JP-A-51-10927, JP-A-54-118247, JP-B-48-3286, JP-B-59-37303, European Patent 280252, etc., styryl dyes described in JP-B-28-3082, JP-B-44-16594, JP-B-59-28898, etc., triarylmethane dyes described in British Patents 446,538 and 1,335,422, JP-A-59-228250, etc., merocyanine dyes described in British Patents 1,075,653, 1,153,341, 1,284,730, 1,475,228 and 1,542,807, etc., and cyanine dyes described in U.S. Pat. Nos. 2,843,486 and 3,294,539, JP-A-62-123454, JP-A-1-291247, etc.

In order to prevent diffusion of these dyes, the following methods are used. For example, ballast groups are introduced into the dyes to give diffusion resistance.

Further, the method of allowing, for example, a hydrophilic polymer having reverse charge to that of a dissociated anionic dye to coexist as a mordant in a layer and localizing the dye in the specified layer by interaction with a dye molecule is disclosed in U.S. Pat. Nos. 2,548,564, 4,124,386 and 3,625,694, etc.

As such hydrophilic polymers, anion conversion polymers are preferred. As the anion conversion polymers, various known quaternary ammonium salt (or phosphonium salt) polymers can be used. The quaternary ammonium salt (or phosphonium salt) polymers are widely known as mordant polymers or antistatic agent polymers in the following publications, etc. They include water-dispersed latexes described in JP-A-59-166940, U.S. Pat. No. 3,958,995, JP-A-55-142339, JP-A-54-126027, JP-A-54-155835, JP-A-53-30328 and JP-A-54-92274, polyvinylpyridinium salts described in U.S. Pat. Nos. 2,548,564, 3,148,061 and 3,756,814, water-soluble quaternary ammonium salt polymers described in U.S. Pat. Nos. 3,709,690, and water-insoluble quaternary ammonium salt polymers described in U.S. Pat. No. 3,898,088.

In order to prevent that they move from a desired layer to another layer or into a processing solution to have photographically undesirable effect, it is particularly preferred that monomers each having at least 2 (preferably, 2 to 4) ethylenic unsaturated groups are copolymerized to use as crosslinked aqueous polymer latexes.

Further, the methods of dying specified layers using water-insoluble dye solids are disclosed in JP-A-56-12639, JP-A-55-155350, JP-A-55-155351, JP-A-63-27838, JP-A-63 -197943, JP-A-2-297543, JP-A-3-167546, JP-A-4-127143, European Patent 15,601, International Patent WO 88/04794, etc.

Furthermore, the methods of dying specified layers using finely divided metal salt grains by which dyes are adsorbed are described in U.S. Pat. Nos. 2,719,088, 2,496,841 and 2,496,843, JP-A-60-45237, etc.

For the purpose of preventing fog or stabilizing photographic performance in the manufacturing processes, during storage or during photographic processing of the photographic materials, various compounds can be contained in the photographic materials. That is, the compounds which can be added include many compounds known as antifogging agents or stabilizers such as azoles, for example, benzothiazolium salts, nitroindazole compounds, chlorobenzimidazole compounds, bromobenzimidazole compounds, mercaptotetrazole compounds, mercaptothiazole compounds, mercaptobenzothiazole compounds, mercaptothiadiazole compounds, aminotriazole compounds, benzothiazole compounds and nitrobenzothiazole compounds; mercaptopyrimidine compounds; mercaptotriazine compounds; thioketo compounds such as oxazolinethione; azaindene compounds such as triazaindene compounds, tetraazaindene compounds (particularly, 4-hydroxy-substituted (1,3,3a,7)tetraazaindene compounds) and pentaazaindene compounds; benzenethiosulfonic acid, benzenesulfinic acid and benzenesulfonic acid amide. Of these, benzotriazole compounds (for example, 5-methylbenzotriazole) and nitroindazole compounds (for example, 5-nitroindazole) are preferred. Further, these compounds may be added to processing solutions. Furthermore, compounds releasing inhibitors during development described in JP-A-62-30243 can be added as stabilizers or for the purpose of preventing black peppers.

The photographic materials can contain developing agents such as hydroquinone derivatives and phenidone derivatives for the various purposes of stabilizers, accelerators, etc.

In the photographic materials, the photographic emulsion layers and other hydrophilic colloid layers may contain inorganic or organic hardening agents. Examples of the hardening agents include chromium salts (chromium alum, chromium acetate, etc.), aldehydes (formaldehyde, glutaraldehyde, etc.), N-methylol compounds (dimethylolurea, etc.), dioxane derivatives, active vinyl compounds (1,3,5-triacryloyl-hexahydro-s-triazine, 1,3-vinylsulfonyl-2-propanol, etc.), active halogen compounds (2,4-dichloro-6-hydroxy-s-triazine) and mucohalogen acids (mucochloric acid, etc.). They can be used alone or in combination.

In the photographic materials, the photographic emulsion layers and other hydrophilic colloid layers may contain hydroquinone derivatives (so-called DIR-hydroquinone) releasing development inhibitors corresponding to the density of images in development.

Examples thereof include compounds described in U.S. Pat. Nos. 3,379,529, 3,620,746, 4,377,634 and 4,332,878, JP-A-49-129536, JP-A-54-67419, JP-A-56-153336, JP-A-56-153342, JP-A-59-278853, JP-A-59-90435, JP-A-59-90436 and JP-A-59-138808.

The photographic materials can contain dispersions of water-insoluble or slightly soluble synthetic polymers for the purpose of dimension stability. For example, polymers having alkyl (meth)acrylates, alkoxyalkyl (meth)acrylates, glycidyl (meth)acrylates or combinations thereof, or combinations thereof with acrylic acid, methacrylic acid, etc. as monomer components can be used.

The silver halide emulsion layers and other layers of the photographic materials preferably contain compounds having acid groups. The compounds having acid groups include organic acids such as salicylic acid, acetic acid and ascorbic acid, and polymers or copolymers having acid monomers such as acrylic acid, maleic acid and phthalic acid as repeating units. With respect to these compounds, the descriptions of JP-A-61-223834, JP-A-61-228437, JP-A-62-25745 and JP-A-62-55642 can be referred to. Of these compounds, for the low molecular weight compounds, ascorbic acid is particularly preferred, and for the polymers, water dispersed latexes of copolymers composed of acid monomers such as acrylic acid and crosslinking monomers each having at least 2 unsaturated groups such as divinylbenzene are particularly preferred.

The silver halide emulsions thus prepared are applied to supports such as cellulose acetate films and polyethylene terephthalate films by the dipping process, the air knife process, the bead process, the extrusion doctor process, the duplicating process, etc.

The supports used in the photographic materials include flexible supports of paper laminated with α-olefin polymers (for example, polyethylene, polypropylene and ethylene/butene copolymer) or synthetic paper, and metals. Of these, polyethylene terephthalate is particularly preferred. Underlayers which can be used in the present invention include underlayers formed using organic solvent systems containing polyhydroxybenzenes, and underlayers formed using aqueous latexes described in JP-A-49-11118, JP-A-52-10491, etc. The underlayers are usually provided after surfaces of the supports have been treated chemically or mechanically. Said treatments include surface activating treatments such as chemical treatments, mechanical treatments and corona discharge treatments.

The present invention can also be utilized in color photographic materials. In this case, various color couplers can be used, wherein the color couplers means compounds which can react with oxidation products of aromatic primary amine developing agents by coupling to produce dyes. Typical examples of the useful color couplers include naphthol or phenol compounds, pyrazolone or pyrazoloazole compounds, and open-chain or heterocyclic ketomethylene compounds. Examples of cyan, magenta and yellow couplers which can be used in the present invention are described in patents cited in *Research Disclosure* (*RD*), 17643, VII-D (December, 1978) and ibid., 18717 (November, 1979).

There is no particular limitation on various additives which can be used in the present invention. For example, ones described in the following corresponding portions can be used.

| Item | Corresponding Portion |
|---|---|
| 1) Chemical Sensitizers | Research Disclosure, 17643, page 23<br>Research Disclosure, 18716, page 648, right column<br>JP-A-2-68539, page 10<br>JP-A-5-313282 |
| 2) Speed Increasing Agents | Research Disclosure, 18716, page 648, right column |
| 3) Spectral Sensitizers Supersensitizers | Research Disclosure, 17643, pages 23 and 24<br>Research Disclosure, 18716, page 649, right column<br>JP-A-2-68539, pages 4–8<br>JP-A-2-12236, page 8<br>JP-A-2-103536, pages 16 and 17<br>JP-A-1-112235<br>JP-A-2-124560<br>JP-A-3-7928<br>JP-A-5-11389 |

-continued

| Item | Corresponding Portion |
|---|---|
| 4) Brightening Agents | Research Disclosure, 17643, page 24 |
| 5) Antifoggants Stabilizers | Research Disclosure, 17643, pages 24 and 25<br>Research Disclosure, 18716, page 649, right column<br>JP-A-2-68539, pages 3, 4, 10 and 11<br>JP-A-2-103536, pages 17 and 18<br>Thiosulfinic acids described in JP-A-1-237538 |
| 6) Light Absorbers Filter dyes UV Absorbers | Research Disclosure, 17643, pages 25 and 26<br>Research Disclosure, 18716, page 649, right column to page 650, left column |
| 7) Stain Inhibitors | Research Disclosure, 17643, page 25<br>Research Disclosure, 18716, page 650, left column to right column |
| 8) Dye Image Stabilizers | Research Disclosure, 17643, page 25 |
| 9) Hardening Agents | Research Disclosure, 17643, page 26<br>Research Disclosure, 18716, page 651, left column<br>JP-A-2-68539, pages 12 and 13<br>JP-A-2-103536, page 18 |
| 10) Binders | Research Disclosure, 17643, page 26<br>Research Disclosure, 18716, page 651, left column<br>JP-A-2-18542, page 3 |
| 11) Color Tone Improvers | JP-A-62-27539, pages 2–10<br>JP-A-3-94249, pages 6–11 |
| 12) Surface Active Agents Antistatic Agents | JP-A-2-68539, pages 11 and 12<br>JP-A-2-12236, page 9<br>JP-A-2-18542, pages 2–4 |
| 13) Matting Agents Lubricants Plasticizers | JP-A-2-68539, pages 12 and 14<br>JP-A-2-103536, page 18 |
| 14) Hydrophilic Colloids | JP-A-68539, page 12 |
| 15) Crossover Cut Methods | JP-A-2-264944, pages 4–14 |
| 16) Dyes Mordants | JP-A-2-68539, pages 13 and 14<br>JP-A-3-24537, pages 14–16<br>JP-A-2-103536, pages 17 and 18<br>Solid dyes described in JP-A-2-294638 and JP-A-3-185773 |
| 17) Polyhydroxybenzenes | JP-A-3-39948, pages 11 and 12<br>Compounds described in European Patent 452772A |
| 18) Hydrazine Nucleating Agents | JP-A-2-12236, pages 2–7<br>JP-A-3-174143, pages 20–27 |
| 19) Nucleating Accelerators | JP-A-2-103536, pages 9–16<br>Compounds described in JP-A-1-179939 |
| 20) Silver Halide Emulsion and the Preparation Thereof | JP-A-2-97937, pages 20 and 21<br>JP-A-2-103536, pages 16 and 17<br>Selenium compounds described in JP-A-5-11389 |
| 21) Polymer Latexes | JP-A-2-103536, page 18 |
| 22) Compounds Having Acid Groups | JP-A-2-103536, page 18 |
| 23) Black Pepper Inhibitor | Compounds described in U.S. Pat. No. 4956257 and JP-A-1-118832 |
| 24) Redox Compounds | Compounds of general formula (I) of JP-A-2-301743<br>JP-A-3-174143, pages 3–20<br>Compounds described in JP-A-5-257239 and JP-A-4-278939 |
| 25) Monomethine Compounds | Compounds of general formula (II) of JP-A-2-287532 |

The present invention is hereinafter described in more detail by reference to examples. However, the present invention is not limited thereto.

EXAMPLE 1

An emulsion was prepared by the following method.

Emulsion

A 0.13M aqueous solution of silver nitrate and an aqueous solution of halogen salts containing $K_2Rh(H_2O)Cl_5$ in an amount corresponding to $1.5\times10^{-7}$ mol per mol of silver, $K_3IrCl_6$ in an amount corresponding to $2\times10^{-7}$ mol, 0.04M potassium bromide and 0.09M sodium chloride were added to an aqueous solution of gelatin containing sodium chloride and 1,3-dimethyl-2-imidazolidine-thione, with stirring at 38° C. for 12 minutes by the double jet method to obtain silver chlorobromide grains having a mean grain size of 0.14 μm and a silver chloride content of 70 mol %, thereby conducting nucleation. Subsequently, a 0.87M aqueous solution of silver nitrate and an aqueous solution of halogen salts containing 0.26M potassium bromide containing $K_3Fe(CN)_6$ in an amount corresponding to $2\times10^{-5}$ mol per mol of silver and 0.65M sodium chloride were similarly added for 20 minutes by the double jet method.

Thereafter, $1\times10^{-3}$ mol of a KI solution was added to each emulsion to conduct conversion, and the resulting emulsion was normally washed with water by the flocculation process. Then, gelatin was added in an amount of 40 g per mol of silver to adjust the emulsion to pH 5.3 and pAg 8.5, and 1 mg of sodium thiosulfate, 1 mg of the following compound (SE-1), 4 mg of chloroauric acid and 10 mg of sodium thiosulfonate were added to conduct chemical sensitization at 55° C. so as to give optimum sensitivity. As a stabilizer, 150 mg of 4-hydroxy-6-methyl-1,3,3a,7-tetraazaindene was added, and 100 mg of proxel was further added as a preservative. The resulting grains were cubic silver iodochlorobromide grains having a mean grain size of 0.25 μm and silver chloride content of 69.9 mol % (coefficient of variation: 10%)

SE-1

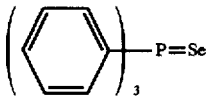

Preparation of Coated Sample

To the resulting emulsion, the following sensitizing dye was added in an amount of $3\times10^{-4}$ mol per mol of silver, and 75 mg of sodium 4,4'-bis(4,6-naphthoxypyrimidine-2-ylamino)stilbenedisulfonate as a supersensitizer, $4\times10^{-4}$ mol of each of the compounds represented by the following (a) and (b), 300 mg of the following hydrazine derivative (c), 200 mg of the following accelerator (d), 100 mg of the following accelerator (e), further a polyethyl acrylate latex, and 1,3-divinylsulfonyl-2-propanol as a hardening agent were added. The emulsion thus prepared was applied to a polyethylene terephthalate film having an undercoat layer provided with a moisture-proof layer containing vinylidene chloride so as to give an amount of silver applied of 3.5 g/m$^2$.

Sensitizing Dye

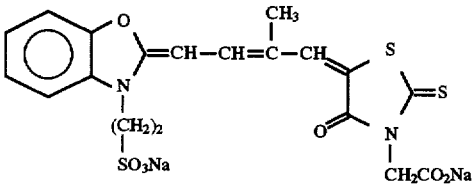

(a)

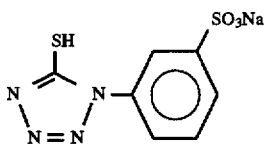

(b)

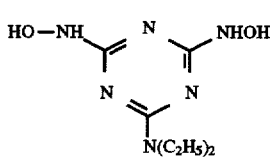

(c)

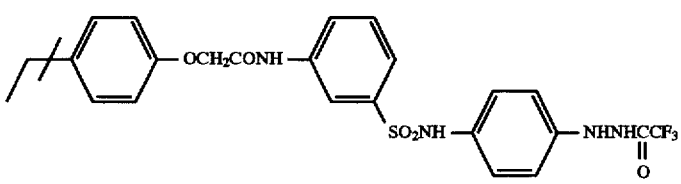

(d)

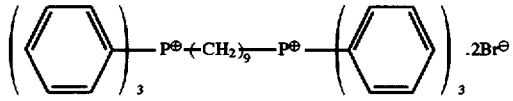

(e)

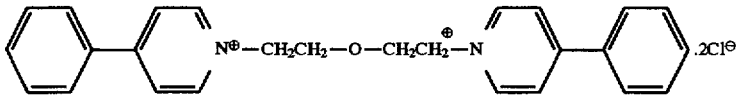

To the emulsion layer, 1.0 g/m$^2$ of gelatin, 40 mg/m$^2$ of an amorphous $SiO_2$ matting agent having a mean grain size of about 3.5 μm, 0.1 g/m$^2$ of methanol silica, 100 mg/m$^2$ of polyacrylamide, 5 mg/m$^2$ of sodium ethylthiosulfonate, 200 mg/m$^2$ of hydroquinone, 20 mg/m$^2$ of silicone oil, and 5 mg/m$^2$of the fluorine surfactant represented by following structural formula (f) and 100 mg/m$^2$ of sodium dodecylbenzenesulfonate as coating aids were applied as a protective layer to prepare a sample.

Further, a back layer and a back protective layer are formed by the following formulation.

(f) $C_8F_{17}SO_2N-\underset{\underset{C_3H_7}{|}}{CH}-COOK$

[Back Layer]

| | |
|---|---|
| Gelatin | 3 g/m$^2$ |
| Latex, Polyethyl Acrylate | 2 g/m$^2$ |
| Surfactant, Sodium p-Dodecylbenzenesulfonate | 40 g/m$^2$ |
| $CH_2=CHSO_2CH_2CONH$ — $(CH_2)_2$ — $CH_2=CHSO_2CH_2CONH$ | 110 mg/m$^2$ |
| $SnO_2$/Sb (weight ratio: 90/10, mean grain size: 0.20 μm) | 200 mg/m$^2$ |
| Dye, Mixture of Dye (g), Dye (h) and Dye (i) | |
| Dye (g) | 50 mg/m$^2$ |
| Dye (h) | 50 mg/m$^2$ |
| Dye (i) | 150 mg/m$^2$ |

-continued

Dye (g)

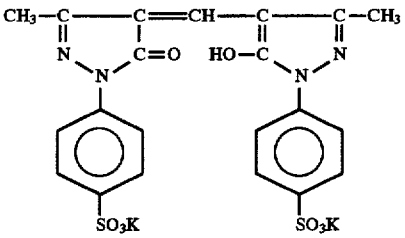

Dye (h)

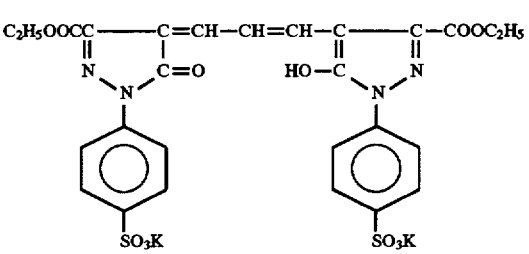

Dye (i)

-continued

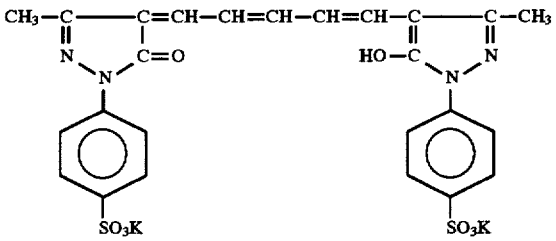

[Back Protective Layer]

| | |
|---|---|
| Gelatin | 0.8 g/m² |
| Finely Divided Polymethyl Methacrylat Grains (mean grain size: 4.5 μm) | 30 mg/m² |
| Sodium Dihexyl-α-sulfosuccinate | 15 mg/m² |
| Sodium p-Dodecylbenzenesulfonate | 15 mg/m² |
| Sodium Acetate | 40 mg/m² |

Composition of Developing Solution

| | |
|---|---|
| Diethylenetriaminepentaacetic Acid | 1.5 g |
| Potassium Carbonate | 50 g |
| Potassium Bromide | 3 g |
| 5-Methylbenzotriazole | 0.1 g |
| 1-Phenyl-5-mercaptotetrazole | 0.02 g |
| Potassium Sulfite | 42 g |
| 4-Hydroxymethyl-4-methyl-1-phenyl-3-pyrazolidone | 0.4 g |
| Developing Agenst Shown in the Following Table 1 | 0.25 mol |

Sodium hydroxide was added to adjust the solution to pH 10.7.

Water was added to adjust the volume to 1 liter.

The samples prepared as described above were exposed to xenon flash light having a light-emitting time of $10^{-5}$ second through an interference filter having a peak at 633 nm and a step wedge. The exposed samples were developed using the above-mentioned developing solution at 35° C. for 30 seconds, followed by fixing, washing and drying. As a fixing solution, GR-F1 (manufactured by Fuji Photo Film Co. Ltd.) was used.

The sensitivity was indicated by a relative value of the reciprocal of the exposure giving a density of 1.5 so that the higher value resulted in the higher density. The sensitivity was indicated by the relative sensitivity taking the sensitivity of Test No. 1 as 100. For the index (γ) representing the contrast of an image, the slope of a straight line connecting the point of fog+density 0.3 and the point of fog+density 3.0 on the characteristic curve is indicated as the γ value. That is, γ=(3.0–0.3)/[log (exposure giving a density of 3.0)–log (exposure giving a density of 0.3)], and the higher γ value shows higher contrast photographic characteristics.

Results are shown in Table 1.

TABLE 1

| No. | Compound Used as Developing Agent | Fog | Sensitivity (S1.5) | Gradation | |
|---|---|---|---|---|---|
| 1 | Hydroquinone | 0.04 | 100 | 23.9 | Comparison |
| 2 | Ascorbic Acid | 0.04 | 85 | 16.9 | Comparison |
| 3 | Example Compound A-1 | 0.04 | 104 | 22.1 | Invention |
| 4 | Example Compound A-5 | 0.04 | 94 | 22.7 | Invention |
| 5 | Example Compound A-8 | 0.04 | 98 | 23.0 | Invention |
| 6 | Example Compound A-13 | 0.04 | 97 | 22.4 | Invention |
| 7 | Example Compound A-17 | 0.04 | 99 | 22.8 | Invention |
| 8 | Example Compound A-25 | 0.04 | 95 | 23.0 | Invention |
| 9 | Example Compound A-27 | 0.04 | 94 | 22.4 | Invention |
| 10 | Example Compound A-42 | 0.04 | 99 | 23.0 | Invention |
| 11 | Example Compound A-45 | 0.04 | 95 | 22.6 | Invention |

<Results>

As shown in Table 1, according to the image forming method using the compounds of the present invention, high-sensitivity, high-contrast images could be obtained in the system in which environmentally, toxicologically preferred enediols were used as the developing agents. Ascorbic acid could not provide a contrast as high as the hydroquinone developing agent, which was unexpected.

EXAMPLE 2

Preparation of Emulsion A

In a reaction vessel, 1200 ml of an aqueous solution of gelatin (containing 18 g of deionized alkali-treated bone gelatin having a methionine content of about 40 μmol/g, pH 4.3) was placed, and each 12 ml portions of solution Ag-1 (containing 20 g of $AgNO_3$, 0.8 g of the gelatin and 0.2 ml of 1 N $HNO_3$ solution per 100 ml) and solution X-1 (containing 6.9 g of NaCl, 0.8 g of the gelatin and 0.3 ml of 1 N NaOH solution per 100 ml) were concurrently added at 24 ml/minute and mixed while keeping the temperature at 38° C. After stirring for 2 minutes, each 20 ml portions of solution Ag-2 (containing 2 g of $AgNO_3$, 0.8 g of the gelatin and 0.2 ml of 1 N $HNO_3$ solution per 100 ml) and solution X-2 (containing 1.4 g of KBr, 0.8 g of the gelatin and 0.2 ml of 1 N NaOH solution per 100 ml) were concurrently added at 31 ml/minute and mixed. After stirring for 2 minutes, each 36 ml portions of solution Ag-1 and solution X-1 were concurrently added at 48 ml/minute and mixed. Then, 20 ml of solution NaCl-1 (containing 10 g of NaCl per 100 ml) was added to adjust the solution to pH 4.8, and the temperature was elevated to 75° C. After ripening for 20 minutes, the temperature was lowered to 60° C., and the pH was adjusted to 5.0. Thereafter, solution Ag-3 (containing 10 g of $AgNO_3$ per 100 ml) and solution X-3 (containing 3.6 g of NaCl per 100 ml) were added at a silver potential of 130 mV by the controlled double jet method. The flow rate at the start of the addition was 7 ml/minute, and 400 ml of solution Ag-3 was added while accelerating the flow rate by 0.1 ml/minute.

Subsequently, 0.059 mol of finely divided AgBr grains having a mean grain size of 0.04 μm was added for 5 minutes. Then, 8.5 cc of a 2 N solution of potassium thiocyanate was added to terminate grain formation.

The resulting grains were rectangular or square tabular grains having (100) faces as main surfaces, and high silver chloride grains having a silver bromide content of 17.3 mol %.

A precipitant was added, and the temperature was lowered to 30° C. After sedimentation washing, an aqueous solution of gelatin was added to adjust the emulsion to pH 6.2 and pCl 3.0 at 38° C. A part of the emulsion was collected, and electron micrographs of the grains were observed. The form characteristics of the grains were as follows:

(The total projected area of (100) tabular grains having an aspect ratio of 2 or more/the sum of projected areas of all AgX grains)=0.91;

Mean aspect ratio of (100) tabular grains having an aspect ratio of 2 or more (mean diameter/mean thickness)=3.7;

Mean diameter of (100) tabular grains having an aspect ratio of 2 or more=0.75 μm;

(The total projected area of (100) tabular grains having an aspect ratio of 2 or more and an edge ratio of 1 to 4/the sum of projected areas of all AgX grains)=0.86;

(When (100) tabular grains having an aspect ratio of 2 or more were taken out up to 70% of the total projected area from larger grains, the coefficient of variation of diameter distribution of the grains)=0.055; and Mean thickness=0.21 μm.

Then, soluble salts were removed by coagulating sedimentation. The temperature was elevated to 40° C. again, and 7.5 g of gelatin, 0.6 g of phenoxyethanol and 0.2 g of sodium polystyrenesulfonate as a viscosity enhancement agent were added. The emulsion was adjusted to pH 6.2 and pAg 7.8 by adding sodium hydroxide.

The following thiosulfonic acid compound-1 was added in an amount of $1\times10^{-5}$ mol/mol of Ag, with stirring the emulsion thus prepared and keeping it at 58° C., and subsequently $8\times10^{-4}$ mol/mol of Ag of the following sensitizing dye-I and $3\times10^{-6}$ mol/mol of Ag of the following sensitizing dye-II were added.

Thiosulfonic Acid Compound-1

$C_2H_5SO_2SNa$

Sensitizing Dye-I

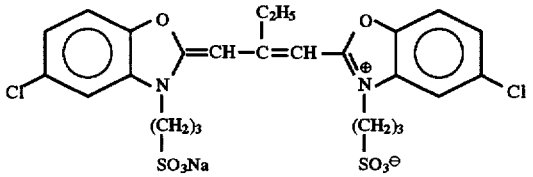

Sensitizing Dye-II

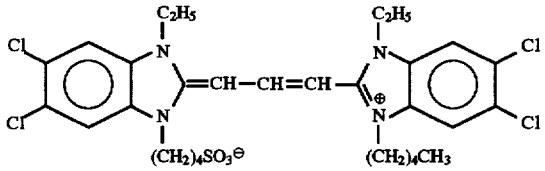

Sodium thiosulfate, the following selenium compound-I, chloroauric acid and potassium thiocyanate were added to most suitably conduct chemical sensitization, followed by cooling to 35° C., thus preparing an emulsion of the present invention.

Selenium Compound-I

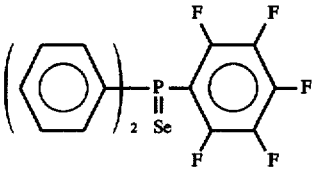

Preparation of Dye Dispersion for Undercoat Layer

The following dye -I was treated with a ball mill by the method described in JP-A-63-197943.

Dye-I

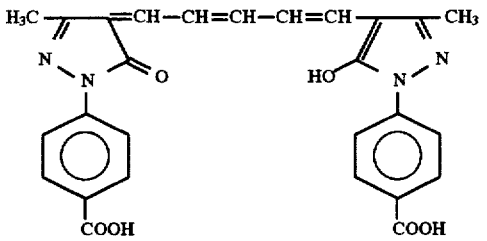

In the 2-liter ball mill, 434 ml of water and 791 ml of a 6.7% aqueous solution of surfactant Triton X-200 (TX-200) were placed, and 20 g of the dye was added to the solution. Then, 400 ml of zirconium oxide ($ZrO_2$) beads (2 mm in diameter) was added, and the contents were pulverized for 4 days. Thereafter, 160 g of 12.5% gelatin was added. After degassing, the ZrO2 beads were removed by filtration. The observation of the resulting dye dispersion showed that the grain size of the pulverized dye was in the wide range of 0.05 to 1.15 μm and the mean grain size was 0.37 μm.

Further, dye grains having a size of 0.9 μm or more were removed by centrifugal separation.

Thus, dye dispersion A was obtained.

Preparation of Support

A 175 μm-thick blue-colored biaxial oriented polyethylene terephthalate film was subjected to corona discharge, and one surface thereof was coated with a first undercoating solution having the following composition with a wire bar coater so as to give an amount coated of 4.9 cc/m², followed by drying at 185° C. for 1 minute.

Then, a first undercoat layer was similarly formed on the opposite side thereof.

| | |
|---|---|
| Butadiene-styrene Copolymer Latex Solution (solid content: 40%, butadiene/styrene ratio by weight = 31–69) | 158 cc |
| 4% Solution of 2,4-Dichloro-6-hydroxy-s-triazine Sodium Salt | 41 cc |
| Distilled Water | 300 cc |

The above-mentioned first undercoat layers on both surfaces were coated with second undercoat layers having the following composition at 165° C. by the wire bar coater system, surface by surface, so as to give the following amounts coated, and dried.

| | |
|---|---|
| Gelatin | 160 mg/m² |
| Dyestuff Dispersion (as the dyestuff solid) | 8 mg/m² |
| $C_{12}H_{25}O(CH_2CH_2O)_{10}H$ | 1.8 mg/m² |
| Proxel | 0.27 mg/m² |
| Matting Agent (polymethyl methacrylate having a mean grain size of 2.5 μm) | 2.5 mg/m² |

Thus, a support having crossover cut layers was prepared.

Preparation of Emulsion Coating Solution

The following agents were added to tabular emulsion A in the following amounts per mol of silver halide to prepare a coating solution.

| | |
|---|---|
| 2,6-Bis(hydroxyamino)-4-diethylamino-1,3,5-triazine | 72 mg |
| Dextran (average molecular weight : 39,000) | 18.5 g |
| Potassium Polystyrenesulfonate (average molecular weight: 600,000) | 1.8 g |
| Gelatin | |
| The amount added was adjusted so as to give an amount of gelatin coated of the emulsion layerof 1.6 g/m$^2$ for each coated sample. | |
| Hardener | |
| 1,2-Bis(vinylsulfonylacetamide)ethane | 3.2 g |
| 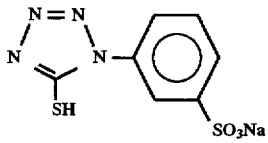 | 34 mg |
| 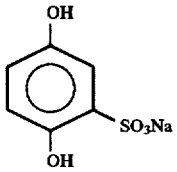 | 34 mg |
| 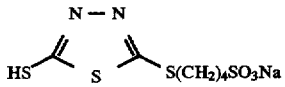 | 70 mg |

A surface protective layer was prepared so as to give the following amounts of respective components.

Coating Solution for Protective Layer

| Coating Solution for Protective Layer | |
|---|---|
| Gelatin | 800 g |
| Dextran (average molecular weight: 39,000) | 200 g |
| $C_{16}H_{33}O(CH_2CH_2O)_{10}H$ | 39 g |
| $C_8F_{17}SO_2N(C_3H_7)(CH_2CH_2O)_4(CH_2)SO_3Na$ | 1.6 g |
| $C_8F_{17}SO_3K$ | 7 g |
| Polymethyl Methacrylate Grains (mean grain size: 3.7 μm) | 91 g |
| Proxel | 0.7 g |
| Sodium Polyacrylate (average molecular weight: 41,000) | 45 g |
| Potassium Polystyrenesulfonate (average molecular weight: 600,000) | 3 g |
| NaOH | 1.6 g |
| $C_8H_{17}C_6H_4(OCH_2CH_2)_3SO_3Na$ | 24 g |
| 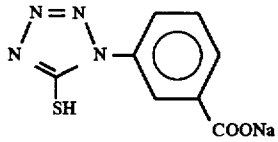 | 0.2 g |
| 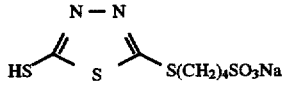 | 0.05 mg |

Distilled water was added to adjust the volume to 14 liters, thus completing a solution.

Preparation of Photographic Material

The emulsion and the coating solution for the surface protective layer previously prepared were successively applied to both sides of the above-mentioned support under the same conditions by the simultaneous extrusion process. The amount of gelatin of the protective layer was adjusted to 0.75 g/m$^2$. The tabular emulsion A was prepared so as to give an amount of silver applied of 1.40 g/m$^2$ per one side of the support (2.8 g/m$^2$ on both sides). Thus, the preparation of a photographic material was completed.

For the resulting photographic material, the swelling rate was measured according to the means and the definition described in JP-A-58-11193. As a result, the swelling rate was 180%.

Further, the crossover light of the above-mentioned photographic material was measured according to the means and the definition described in U.S. Pat. Nos. 4,425,425 and 4,425,426. As a result, it was 19%.

| Preparation of Developing Solution | |
|---|---|
| Potassium Sulfite | 30.0 g |
| Potassium Carbonate | 55.2 g |
| Diethylene Glycol | 10.0 g |
| Diethylenetriaminepentaacetic Acid | 2.0 g |
| Sodium Bromide | 3.0 g |
| 5-Methylbenzotriazole | 0.1 g |
| 4-Hydroxymethyl-4-methyl-1-phenyl-3-pyrazolidone | 2.0 g |
| Monomethylhydroxylamine Hydrochloride | 8.4 g |
| Developing Agents Shown in the following Table 2 | 0.25 mol/liter |

Sodium hydroxide was added to adjust the solution to pH 9.5, and water was added to adjust the volume of a solution for use to 1 liter.

In a 2000-ml beaker, 1000 ml of the developing solution was placed, and the beaker was covered with Saran Wrap (manufactured by Asahi Chemical Industry Co., Ltd.). The cover was perforated to form holes having a diameter of 2 mm, and the solution was allowed to stand for 7 days at room temperature. This was used as an aged solution. As a fixing solution, SR-F1 manufactured by Fuji Photo Film Co. Ltd. was used. Development processing was conducted with a CEPROS-M manufactured by Fuji Photo Film Co. Ltd., using a fresh solution and the aged solution allowed to stand for 7 days at room temperature of the above-mentioned developing solution, for 47 seconds at dry to dry with keeping the development temperature and the fixing temperature at 35° C.

With respect to evaluation of the photographic characteristics, both sides of the photographic material were exposed for 0.05 second using an X-ray orthoscreen, HR-4, manufactured by Fuji Photo Film Co. Ltd. After exposure, the following processing was conducted to evaluate sensitivity. The gradation was indicated by a value obtained by dividing the difference between fog+a density of 0.25 and fog+a density of 0.2 by the difference between the logarithms of the exposures giving the respective densities. The sensitivity was relatively indicated, taking as 100 the reciprocal of the exposure required to obtain fog+a density of 1.0 when the photographic material was processed with the fresh developing solution containing no added compound. Results of the photographic characteristics are shown in Table 2.

TABLE 2

| No. | Compound Used as Developing Agent | Fresh or Aged Solution | Photographic Characteristics Sensitivity | Photographic Characteristics Gradation | |
|---|---|---|---|---|---|
| 1 | Ascorbic Acid | Fresh | 100 | 2.7 | Comparison |
| | | Aged | 60 | 1.8 | |
| 2 | Example Compound A-1 | Fresh | 100 | 2.7 | Invention |
| | | Aged | 84 | 2.3 | |
| 3 | Example Compound A-5 | Fresh | 98 | 2.6 | Invention |
| | | Aged | 83 | 2.4 | |
| 4 | Example Compound A-9 | Fresh | 100 | 2.6 | Invention |
| | | Aged | 86 | 2.5 | |
| 5 | Example Compound A-20 | Fresh | 98 | 2.7 | Invention |
| | | Aged | 89 | 2.5 | |
| 6 | Example Compound A-32 | Fresh | 98 | 2.7 | Invention |
| | | Aged | 86 | 2.4 | |
| 7 | Example Compound A-34 | Fresh | 101 | 2.7 | Invention |
| | | Aged | 92 | 2.6 | |
| 8 | Example Compound A-48 | Fresh | 99 | 2.7 | Invention |
| | | Aged | 83 | 2.5 | |
| 9 | Example Compound A-49 | Fresh | 100 | 2.7 | Invention |
| | | Aged | 90 | 2.5 | |
| 10 | Example Compound A-50 | Fresh | 100 | 2.7 | Invention |
| | | Aged | 84 | 2.4 | |
| 11 | Example Compound A-55 | Fresh | 100 | 2.6 | Invention |
| | | Aged | 86 | 2.4 | |

The photographic characteristics of the fresh solutions and the aged solutions of the developing solutions are shown in Table 2. The aging photographic characteristics of the developing solution of the compounds of the present invention are good in both the sensitivity and the gradation. The developing solution of ascorbic acid significantly reduces the sensitivity in the aging photographic characteristics, and enhances soft contrast for the gradation. These results are difficult to be easily expected.

Use of the compounds of the present invention as the developing agents makes it possible to provide stable, good-quality images without use of the dihydroxybenzene compounds as the developing agents, and particularly to provide super hard negative images using the photographic materials containing the hydrazine compounds.

While the invention has been described in detail and with reference to specific embodiments thereof, it will be apparent to one skilled in the art that various changes and modifications can be made therein without departing from the spirit and scope thereof.

What is claimed is:

1. A method for processing a silver halide photographic material comprising processing the silver halide photographic material exposed with a developing solution containing at least one kind of developing agent represented by the following general formula (A):

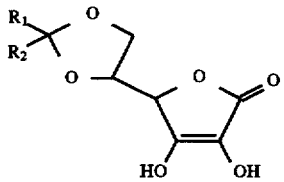

(A)

wherein $R_1$ and $R_2$ may be the same or different, and each represents a hydrogen atom or a substituent group, with the proviso that $R_1$ and $R_2$ are not methyl groups at the same time nor a combination of a hydrogen atom and a methyl group.

2. A method for processing a silver halide photographic material containing a hydrazine nucleating agent, comprising processing the silver halide photographic material exposed with a developing solution containing at least one developing agent represented by the following formula (A):

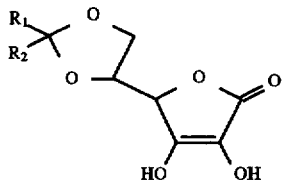

(A)

wherein $R_1$ and $R_2$ may be the same or different, and each represents a hydrogen atom or a substituent group, with the proviso that $R_1$ and $R_2$ are not methyl groups at the same time nor a combination of a hydrogen atom and a methyl group.

3. The method for processing a silver halide photographic material containing a hydrazine nucleating agent as claimed in claim 2, wherein said developing solution further comprises (a) 0.1 mol/liter or more of a sulfite, and (b) a 1-phenyl-3-pyrazolidone auxiliary developing agent and/or an aminophenol auxiliary developing agent, and does not substantially contain a dihydroxybenzene compound.

4. The method for processing a silver halide photographic material containing a hydrazine nucleating agent as claimed in claim 2, wherein said silver halide photographic material further comprises a nucleating accelerator.

5. A method for processing a silver halide photographic material containing a tabular silver halide emulsion, comprising processing the silver halide photographic material exposed with a developing solution containing at least one developing agent represented by the following formula (A):

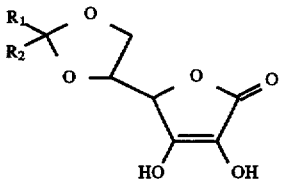

(A)

wherein $R_1$ and $R_2$ may be the same or different, and each represents a hydrogen atom or a substituent group, with the proviso that $R_1$ and $R_2$ are not methyl groups at the same time nor a combination of a hydrogen atom and a methyl group.

* * * * *